(12) United States Patent
Michalak et al.

(10) Patent No.: US 11,931,515 B2
(45) Date of Patent: Mar. 19, 2024

(54) METHOD FOR USING A FACE STRIP FOR TREATING BREATHING CONDITIONS

(71) Applicant: SomniFix International LLC, Washington, DC (US)

(72) Inventors: Nicholas Michalak, McLean, VA (US); Andre Michalak, McLean, VA (US)

(73) Assignee: SomniFix International LLC, Washington, DC (US)

( * ) Notice: Subject to any disclaimer, the term of this patent is extended or adjusted under 35 U.S.C. 154(b) by 574 days.

(21) Appl. No.: 16/759,664

(22) PCT Filed: Oct. 26, 2018

(86) PCT No.: PCT/US2018/057828
§ 371 (c)(1),
(2) Date: Apr. 27, 2020

(87) PCT Pub. No.: WO2019/084482
PCT Pub. Date: May 2, 2019

(65) Prior Publication Data
US 2020/0306482 A1 Oct. 1, 2020

Related U.S. Application Data

(60) Provisional application No. 62/578,048, filed on Oct. 27, 2017, provisional application No. 62/578,043, (Continued)

(51) Int. Cl.
*A61M 16/06* (2006.01)
*A61M 16/10* (2006.01)

(52) U.S. Cl.
CPC .... *A61M 16/0688* (2014.02); *A61M 16/0616* (2014.02); *A61M 16/1065* (2014.02); (Continued)

(58) Field of Classification Search
CPC .......... A61M 16/0688; A61M 16/0616; A61M 16/1065; A61M 2016/0661; (Continued)

(56) References Cited

U.S. PATENT DOCUMENTS 2,574,623 A 11/1951 Clyde
2,922,418 A 1/1960 Heffernan et al.
(Continued)

FOREIGN PATENT DOCUMENTS

AU 2018225735 A1 9/2019
DE 29721589.9 U1 2/1998
(Continued)

OTHER PUBLICATIONS

International Search Report and Written Opinion, PCT/US2018/057828, Somnifix International LLC (dated Jan. 16, 2019).
(Continued)

*Primary Examiner* — Valerie L Woodward
(74) *Attorney, Agent, or Firm* — Foley & Lardner LLP

(57) ABSTRACT

A method for treating a breathing condition includes providing a face strip having an adhesive layer and a mesh layer disposed on the adhesive layer and applying the adhesive layer to a mouth of a patient diagnosed with a breathing condition including at least one of a dry mouth, a sore throat, nasal congestion, or hypoxia. The method further includes covering the patient's mouth with the face strip and providing resistance from the face strip at the patient's mouth, and increasing nasal respiration with the face strip. The face strip reduces or prevents the incidence of the breathing condition.

17 Claims, 19 Drawing Sheets

Related U.S. Application Data filed on Oct. 27, 2017, provisional application No. 62/578,051, filed on Oct. 27, 2017.

(52) U.S. Cl.
CPC ............... *A61M 2016/0661* (2013.01); *A61M 2210/0625* (2013.01)

(58) Field of Classification Search
CPC . A61M 2210/0625; A61F 5/0006; A61F 5/56; A61F 5/566; A63B 23/03; A63B 23/18; A63B 71/085; A63B 2071/086; A63B 2071/088
See application file for complete search history.

(56) References Cited

U.S. PATENT DOCUMENTS

| | | | |
|---|---|---|---|
| 2,928,388 | A | 3/1960 | Jaroslaw |
| 4,004,584 | A | 1/1977 | Geaney |
| 4,240,420 | A | 12/1980 | Riaboy |
| 4,354,489 | A | 10/1982 | Riaboy |
| 4,711,237 | A | 12/1987 | Kaiser |
| 4,817,636 | A | 4/1989 | Woods |
| 4,825,881 | A | 5/1989 | Bessler |
| 5,154,706 | A * | 10/1992 | Cartmell ............ A61F 13/00085 128/850 |
| 5,392,773 | A | 2/1995 | Bertrand |
| 6,076,526 | A | 6/2000 | Abdelmessih |
| 6,089,232 | A | 7/2000 | Portnoy et al. |
| 6,148,820 | A * | 11/2000 | Herrin ....................... A61F 5/56 2/9 |
| 6,405,729 | B1 | 6/2002 | Thornton |
| 6,494,209 | B2 | 12/2002 | Kulick |
| 7,451,766 | B2 | 11/2008 | Miller |
| 8,991,399 | B2 | 3/2015 | Michalak |
| 9,795,175 | B2 | 10/2017 | Michalak |
| 2003/0149387 | A1* | 8/2003 | Barakat ...................... A61F 5/56 602/45 |
| 2004/0089310 | A1 | 5/2004 | Portnoy |
| 2005/0178392 | A1 | 8/2005 | Tinsley |
| 2006/0070629 | A1 | 4/2006 | Haddix et al. |
| 2008/0004137 | A1 | 1/2008 | Kasashima et al. |
| 2008/0041397 | A1 | 2/2008 | Hirs |
| 2008/0302370 | A1 | 12/2008 | Hirs |
| 2009/0050144 | A1 | 2/2009 | Pierce et al. |
| 2009/0283100 | A1 | 11/2009 | Hirs |
| 2009/0302370 | A1 | 12/2009 | Guha et al. |
| 2011/0212811 | A1* | 9/2011 | Rutten .................... A63B 23/18 482/13 |
| 2011/0290256 | A1 | 12/2011 | Sather et al. |
| 2012/0000472 | A1 | 1/2012 | Martucci |
| 2014/0251335 | A1* | 9/2014 | Black ................ A61M 16/0616 128/206.25 |
| 2014/0360502 | A1* | 12/2014 | Kushida ............ A61M 16/0694 128/206.25 |
| 2016/0165972 | A1* | 6/2016 | Michalak ................ A61B 50/30 128/848 |
| 2016/0302961 | A1* | 10/2016 | Seaman ...................... A61F 5/56 |
| 2017/0028162 | A1 | 2/2017 | Leeflang et al. |

FOREIGN PATENT DOCUMENTS

| | | |
|---|---|---|
| JP | 61-008011 U | 1/1986 |
| JP | S61-008011 U | 1/1986 |
| JP | 3060915 U | 9/1999 |
| JP | 2003-159269 A | 6/2003 |
| JP | 2003-190200 A | 7/2003 |
| JP | 2004-505669 A | 2/2004 |
| JP | 2005-007104 A | 1/2005 |
| JP | 3132717 U | 5/2007 |
| JP | 3150431 U | 5/2009 |
| JP | 2014-236928 A | 12/2014 |
| JP | 2016-527976 A | 9/2016 |
| WO | WO-2015/017862 A1 | 2/2015 |

OTHER PUBLICATIONS

Office Action on U.S. Appl. No. 16/488,167 dated Sep. 28, 2021, 12 pages.
Examination Report on BR Patent App. No. 112016002362-5 dated Jun. 28, 2022, 6 pages (with translation).
"Snore-Seal: Disposable Anti-Snoring Strips", Bradley Scott Medical, Inc., 2009, retrieved online from http://snoreseal.com/index.htm.
Examination Report for BR Patent App. No. 112016002362-5 dated Feb. 8, 2022, 7 pages (with translation).
Examination Report on AU Patent App. No. 2018201370 dated Oct. 29, 2019, 3 pages.
Examination Report on AU Patent App. No. 2018355548 dated Aug. 9, 2021, 5 pages.
Examination Report on EP Patent App. No. 14832141.7 dated Jul. 24, 2020, 4 pages.
Examination Report on EP Patent App. No. 14832141.7 dated Jun. 10, 2022, 4 pages.
Extended European Search Report for European Patent App. No. 14832141.7 dated Mar. 31, 2017, 6 pages.
Final Office Action on U.S. Appl. No. 16/488,167 dated Mar. 23, 2022, 11 pages.
Further Examination Report on NZ Patent App. No. 717510 dated Nov. 22, 2019, 4 pages.
International Search Report & Written Opinion for PCT/US2014/049634 dated Nov. 19, 2014.
Japanese Office Action for Japanese Patent App. No. JP 2018-231587, dated Sep. 10, 2019, 6 pages (with translation).
Non-Final Office Action on U.S. Appl. No. 15/789,179 dated Feb. 19, 2020.
Notice of Allowance on U.S. Appl. No. 15/482,272 dated Feb. 10, 2020, 2 pages.
Notice of Allowance on U.S. Appl. No. 15/482,272 dated Oct. 11, 2019, 7 pages.
Notice of Allowance on U.S. Appl. No. 15/789,179 dated Jun. 24, 2020, 7 pages.
Notice of Reasons for Refusal for JP Patent App. No. 2021-038140 dated Mar. 8, 2022, 8 pages (with translation).
Office Action for Japanese Patent App. No. 2018-231587 dated Apr. 14, 2020, 5 pages (with translation).
Office Action for Japanese Patent App. No. 2018-231587 dated Nov. 10, 2020, 4 pages (with translation).
Office Action for JP Patent App. No. 2016-531949, dated Jun. 12, 2018, 12 pages (with translation).
Office Action KR Patent App. No. 10-2016-7005671, dated Jan. 22, 2021, 6 pages (with translation).
Office Action on AU Patent App. No. 2018201370 dated Apr. 2, 2020, 3 pages.
Office Action on CA Patent App. No. 2890308 dated Sep. 23, 2020, 3 pages.
Office Action on CA Patent App. No. 3080556 dated Mar. 18, 2022, 5 pages.
Office Action on IL Patent App. No. 243909 dated Jun. 10, 2019, 6 pages (with translation).
Office Action on IL Patent App. No. 243909 dated Mar. 17, 2020, 5 pages (with translation).
Office Action on Indonesian Patent App. No. P00201601364 dated Jun. 12, 2019, 2 pages (no translation available).
Office Action on JP Patent App. No. 2019-567496, dated Dec. 21, 2021, 8 pages (with translation).
Office Action on JP Patent App. No. 2021-038140 dated Aug. 17, 2021, 8 pages (with translation).
Office Action on U.S. Appl. No. 15/482,272 dated Jun. 27, 2019, 7 pages.
Search Report & Written Opinion on BR Patent App. No. 112016002362-5 dated Feb. 11, 2020, 7 pages (including translation).
Examination report No. 2 for Australian Patent App. No. 2018355548 dated Aug. 9, 2021, 5 pages.
Office Action for Canadian Patent App. No. 3,080,556 dated Dec. 2, 2022, 10 pages.

(56) References Cited

OTHER PUBLICATIONS

Office Action for Canadian Patent App. No. 3,134,350 dated Jan. 23, 2023, 4 pages.
Examination Report on AU Appl. Ser. No. 2018225735 dated Jun. 5, 2020 (3 pages).
Examination Report on AU Appl. Ser. No. 2018355548 dated Aug. 13, 2020 (5 pages).
Examination Report on NZ Appl. Ser. No. 756676 dated Jun. 2, 2021 (3 pages).
International Preliminary Report on Patentability on Appl. Ser. No. PCT/US2018/019226 dated Sep. 6, 2019 (9 pages).
International Search Report & Written Opinion on Appl. Ser. No. PCT/US2018/019226 dated May 8, 2020 (11 pages).
Office Action on CA Appl. Ser. No. 3054554 dated Jan. 3, 2020 (4 pages).
Office Action on CA Appl. Ser. No. 3054554 dated Mar. 12, 2021 (3 pages).
Office Action on CA Appl. Ser. No. 3054554 dated Aug. 10, 2020 (3 pages).
Office Action on CA Appl. Ser. No. 3054554 dated Aug. 18, 2021 (3 pages).
Office Action on CA Appl. Ser. No. 3080556 dated Jul. 5, 2021 (3 pages).

* cited by examiner

METHOD FOR USING A FACE STRIP FOR TREATING BREATHING CONDITIONS

CROSS-REFERENCE TO RELATED APPLICATIONS

The present application is a National Stage Application of PCT/US2018/057828, filed Oct. 26, 2018, which claims the benefit of and priority to U.S. Provisional Patent Application No. 62/578,043, filed Oct. 27, 2017, U.S. Provisional Patent Application No. 62/578,048, filed Oct. 27, 2017, and U.S. Provisional Patent Application No. 62/578,051, filed Oct. 27, 2017, the entire disclosures of which are hereby incorporated by reference.

BACKGROUND

The present application relates to various methods of using a face strip covering at least a portion of a user's mouth in order to promote breathing through the user's nose (i.e., nasal respiration) rather than or in addition to breathing through the user's mouth (i.e., oral respiration). For example, the face strip is applied directly to the user's lips and restricts the flow of air into and out of the user's mouth as the user breathes. This resistance causes the user to naturally compensate for the lack of airflow through his or her mouth by breathing through the user's nose (e.g., nostrils), diverting around the user's mouth and allowing the user to keep his or her mouth in a closed position.

Various conditions are caused by a user predominantly or exclusively breathing through his or her mouth for extended periods of time. For example, such conditions may include dry mouth (xerostomia), sore throat, nasal congestion, and/or low oxygen (hypoxia). These and other conditions are often exacerbated when an individual sleeps with his or her mouth open, resulting in predominantly-mouth breathing for extended periods of time (e.g., between approximately 6-8 hours per day).

Some breathing conditions may be treated by wearing expensive, uncomfortable devices that affect a user's breathing. For example, a continuous positive air pressure ("CPAP") device may be used to treat sleep apnea by providing a positive pressure at a user's mouth and/or nose in order to widen the user's airway. However, CPAP devices require a mask to be held in place and sealingly engage a user's face in order to maintain pressurization, with a strap extending behind the user's head. The contact from the mask and the strap may be uncomfortable, further disrupting a user's sleep. Further, hoses extending from the mask limit the ability of a user to reposition while sleeping and particularly restricts the ability for a user to sleep face down on a bed, without affecting the mask seal. Finally, a CPAP device is an active system and requires power to operate, which limits where the device may be used and makes it more difficult to take while traveling.

Other breathing conditions may be treated with oral appliance therapy ("OAT"), which utilizes a mandibular advancement device ("MAD") to hold the jaw in a position that reduces airway collapse. As with CPAP devices, a MAD may be uncomfortable for a user and restrict the ability of the user to reposition comfortably while sleeping.

It should be understood that MAD and CPAP devices generally hold the mouth at least partially open, which exacerbates conditions, including dry mouth, sore throat, nasal congestion, among other conditions. For example, the movement of the user's jaw with a MAD and the pressurized airflow from the CPAP device each contribute to forcing the user's mouth to open. It would therefore be advantageous to provide a device capable of externally maintaining the lips and jaw of the face of a user in a relaxed, closed position, in order to facilitate respiration through the nasal passages. Such a device could be used either alone or in combination with a device for treating sleep apnea which, as a side effect, causes or exacerbates any of these conditions. For example, such a device may be paired with MAD and CPAP devices to correct the deficiencies of these devices.

It may be further advantageous to provide resistance to one or more or mouth or nasal respiration as part of an exercise or training regimen. For example, hypercapnia training utilizes temporary, non-toxic restrictions of oxygen in order to prepare a user for similar conditions experienced in high altitudes or underwater (e.g., with a closed-circuit re-breather). Alternatively, breathing resistance may be used as a facet of endurance and/or stamina training, to exercise a user's diaphragm and improve a user's lung capacity. Such face strip discussed may be used to prepare for these or other conditions.

SUMMARY

The following presents a general summary of aspects of the present disclosure in order to provide a basic understanding of the disclosure. This summary is not an extensive overview of the disclosure and is not intended to identify key or critical elements of the invention or to delineate the scope of the present disclosure. The following summary merely presents some concepts of the present disclosure in a general form as a prelude to the more detailed description provided below.

The present disclosure relates to methods for treating and preventing dry mouth in a user using a face device (i.e., a face strip, sleep-aid device, resistance device, etc.) configured to hold a user's mouth in a naturally closed position such that the tongue and jaw of the user will not relax during sleep and cause pauses in breathing. The face device is a face strip, which, according to one example, includes a hypoallergenic adhesive affixed to a paper-thin, perforated silicone or cloth (e.g., polyester) mesh layer, such that the device is securely and temporarily affixed to the face of a user (e.g., the cheeks, lips, and/or jaw of the user). As a specific example, the face strip is configured to be securably attachable to an external portion of the lips of the user such as the upper lip vermillion, the lower lip vermillion, or a combination of both. The face strip according to the present disclosure is configured to hold the lips of the user closed, promoting the user to breathe through the nasal passages and nostrils. Certain patient populations, such as those suffering from dry mouth, sore throat, nasal congestion, and/or low oxygen, but not any sleep disorder (such as apnea or snoring) may benefit from the face strip.

The face strip includes an adhesive layer having an opening configured to provide an alternate channel for respiration through a mouth of a user during use of the face strip in an event that one or more nasal passages of the user become blocked, forcing the user to breathe through the mouth. The opening is disposed on a location on the adhesive layer and is configured to overlay the mouth of the user during use of the face strip. The face strip also includes a permeable mesh layer, which includes a mesh disposed over the adhesive layer such that the permeable mesh layer covers at least a portion of a surface of the adhesive layer and covers the opening in the adhesive layer.

The face strip is preferably configured to conform to the shape of the user's face, and provide a semi-secure seal over the mouth of the user during use. While the seal need not be completely air-tight, any restriction over the mouth of a user during sleep will help to curtail his or her use of the mouth to breathe (e.g., oral respiration).

When the face strip is properly positioned and affixed to the face of the user, the user's respiration is channeled, and therefore encouraged to flow through the nasal passages of the user rather than through the mouth. Through this method of nasal respiration, it is less likely for the user to suffer from a dry mouth, sore throat, nasal congestion, and/or low oxygen.

In some embodiments, a method for preventing or treating at least one of a dry mouth, sore throat, nasal congestion, or hypoxia is disclosed. The method includes, prior to sleeping or engaging in a controlled respiratory activity, affixing a face strip, including a flexible pad having a front side and back side over a mouth of a user diagnosed at least one of these conditions. Use of the face strip reduces incidence of condition in the user compared to the user not using the face strip.

In some embodiments, the method for treating each of these conditions includes maintaining an upper lip and a lower lip of a face of a user in a closed position, affixing a face strip to at least one of an upper vermillion and a lower vermillion of the user, such that the upper lip, the lower lip, and a mouth of the user are substantially covered by the face strip, ensuring that a tongue of the user does not relax during sleep, forming a semi-secure seal over the mouth of the user with the face strip, and reducing an incidence of the corresponding condition in the user. The face strip further holds the mouth of the user in a naturally closed posture and thereby facilitates nasal respiration by the user.

In some embodiments, a method of using the face strip to treat or prevent a breathing condition may be used while a user is simultaneously undergoing treatment for sleep apnea or snoring using a CPAP device or MAD. For example, a sleep "mask" is disclosed in U.S. Pat. No. 8,991,399, the disclosure of which is incorporated by reference herein in its entirety. A combination of a face sleep strip and a CPAP machine or a MAD for treating sleep apnea and snoring is disclosed in U.S. provisional application Ser. No. 62/463,425, the disclosure of which is incorporated herein by reference in its entirety.

In some embodiments, a method of endurance training includes applying a face strip to the user's mouth and breathing through an opening in the face strip, including as the user's heart rate increases. The opening in the face strip restricts the flow of air into and out of the user's lungs, promoting a hypercapnia training regimen.

DETAILED DESCRIPTION

Figure 1:
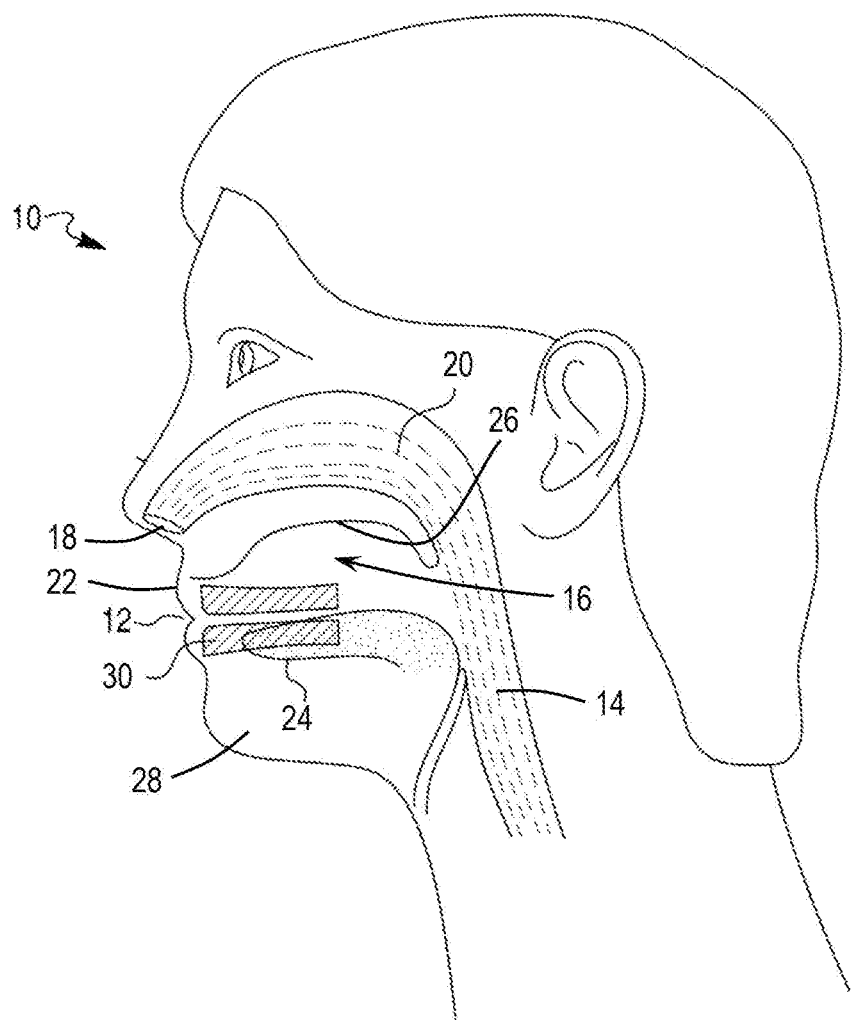
FIG. 1 is a side view of a MAD in position in the mouth of a user during sleep while the user's lips are in a closed position.

The present disclosure is capable of embodiments in many different forms, and there are shown in the drawings, and will herein be described in detail, certain embodiments with the understanding that the present disclosure is to be considered exemplary and is not intended to limit the broad aspects of the invention to the embodiments illustrated and described.

Referring now to FIG. 1, a user 10 is shown with an example of a MAD positioned in the user's mouth 12. Specifically, a user's airway 14 is connected to the mouth 12 at a mouth cavity 16 and also connects to a user's nostrils 18 through a nasal passage 20. As shown in FIG. 1, a user's lips 22 are shown in a closed position and a tongue 24 is lowered away from an upper palate 26 at the top of the mouth 12.

As shown in FIG. 1, an example of a MAD 30 is positioned in the mouth cavity 16 of a user 10. Because the user's lips 22 are closed, air bypasses the mouth cavity 16 and instead flows through the nasal passage 20, between the nostrils 18 and the airway 14. Alternatively, the tongue 24 may be pressed against the upper palate 26, similarly directing air to the nasal passage 20, such that the user can breathe through his or her nostrils 18 and nasal passage 20.

A MAD 30 is an oral appliance apparatus configured to treat snoring and obstructive sleep apnea by inserting the MAD 30 into the mouth 12 of a user 10 while the user 10 sleeps. A MAD 30 is generally made of a hard acrylic material, although in some cases, the MAD 30 may be made of a softer material. A MAD 30 is customizable to fit and engage upper and lower teeth of a particular user 10 and is configured to hold a jaw 28 of the user slightly forward (e.g., away from the airway) from its natural resting position, such that the airway 14 remains more open during sleep. Specifically, as the lower jaw 28 shifts forward, the user's tongue 24 shifts forward, putting less force on the airway 14 and further opening the airway 14 to promote clearer breathing through the nasal passage 20.

The MAD 30 may be formed of a variety of materials and configured to be disposed in variation locations in the mouth 12. For example, a PM Positioner™ is formed of an acrylic material and has an adjustment mechanism disposed on a cheek side of the device near a user's molars when the device is worn by the user 10. As another example, the SomnoDent® SUAD™ is formed of an acrylic material reinforced by a metal framework and has an adjustment mechanism which includes two elastic bands and which keeps the jaw 28 from falling open (e.g., away from the upper palate 26) while the user 10 is sleeping. As another example, a SomnoDent® MAD is formed of an acrylic material and has a recessed screw mechanism on each side of an upper part and ball clasps which hold the device in position. As another example, an EMA® (Elastic Mandibular Advancement) device is formed of a plastic material and has an upper part and a lower part connected to the upper part by rubber straps on sides of the device; by using differently sized straps, the device may be positioned differently while in use. As another example, a TAP® (Thornton Adjustable Positioner) is a device formed of a nickel-free, material reinforced by a cobalt-chromium hardware and has a hook and socket mechanism which holds an upper tray and a lower tray together; the device's position is adjustable. As another example, a Herbst Appliance is formed of acrylic, thermal active, and soft materials and has a post and sleeve mechanism to advance a jaw 28 of a user 10 and a ball and hook mechanism such that a vertical opening degree is adjustable.

However, these and other MADs 30 are ineffective if the tongue 24 of a user 10 does not remain sealed against the upper palate 26. Even though the lips 12 remain in the closed position, because the tongue 24 is not sealing the mouth cavity 16 from the airway 14 and the nasal passage 20, and during nasal respiration, some air passes from the nasal passage 20, into the mouth cavity 16, and then back into the airway 14. This airflow provides some oral respiration, which, when prolonged, can cause dry mouth and contribute to other breathing conditions described above.

Figure 2:
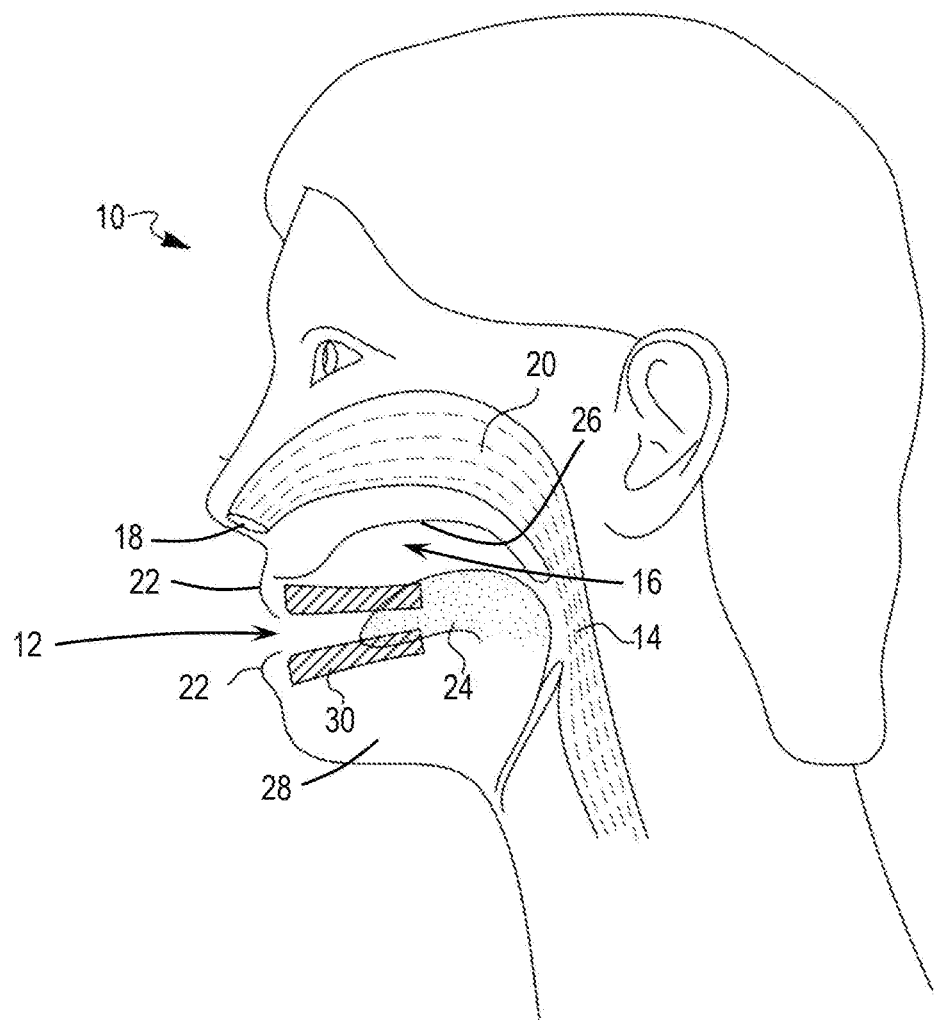
FIG. 2 is a side view of a MAD in position in the mouth of a user during sleep while the user's lips are in an open position.
Figure 3:
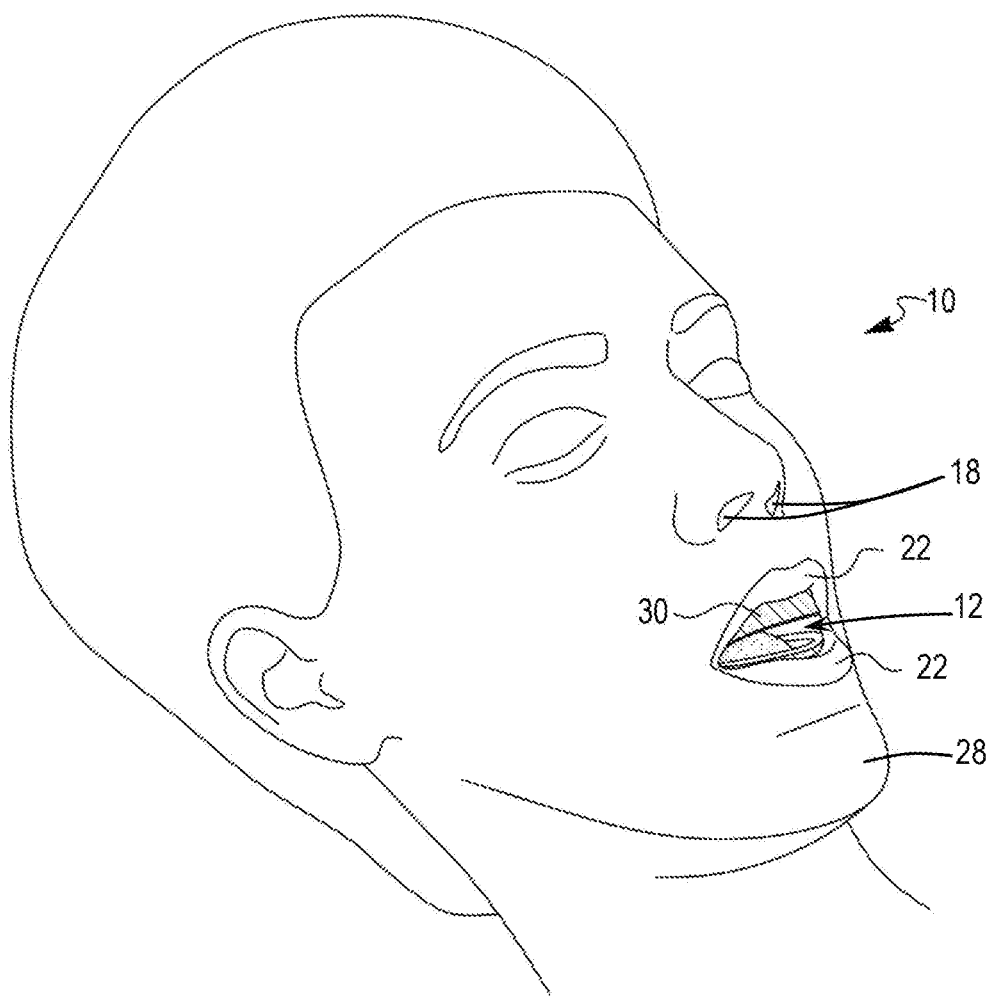
FIG. 3 is a perspective view of a MAD in position in the mouth of a user during sleep while the user's lips are in an open position.

Alternatively, referring to FIGS. 2 and 3, the user's lips 22 are shown in an open position. Specifically, while a MAD 30 is configured to orient a user's jaw 28 in a forward direction in order to open up the airway 14, it may also bias the jaw 28 downward toward an open position. This interference due to the MAD 30 in the user's mouth 12 makes it more difficult for the user 10 to naturally close his or her mouth 12 over or around a MAD 30, resulting in the separation of the lips 12 to the open position (i.e., lip incompetence). Lip incompetence leads to a breathing pattern through the mouth that results in a loss of a seal between the tongue 24 and the upper palate 26. As shown in FIGS. 2 and 3, when the user's tongue 24 unseals from the upper palate 26, the tongue 24 slides rearward in the mouth 12, away from the user's lips 22. As the tongue 24 slides rearward, it presses into the airway 14, once again restricting airflow through the airway 14. For example, the tongue 24 may block the nasal passage 20, directing substantially all of the airflow through the mouth 12 for oral respiration. Alternatively, the user 10 may overcompensate for the restriction in the airway 14 by employing both oral and nasal respiration to restore stable breathing patterns. As discussed above, dry mouth may be caused due to prolonged oral respiration. Unless a user of a MAD 30 has another individual present who can inform the user 10 of breathing conditions which lead to dry mouth, the user 10 will further be oblivious to when those breathing conditions occur while sleeping and will otherwise be unable to remedy the conditions.

Figure 4:
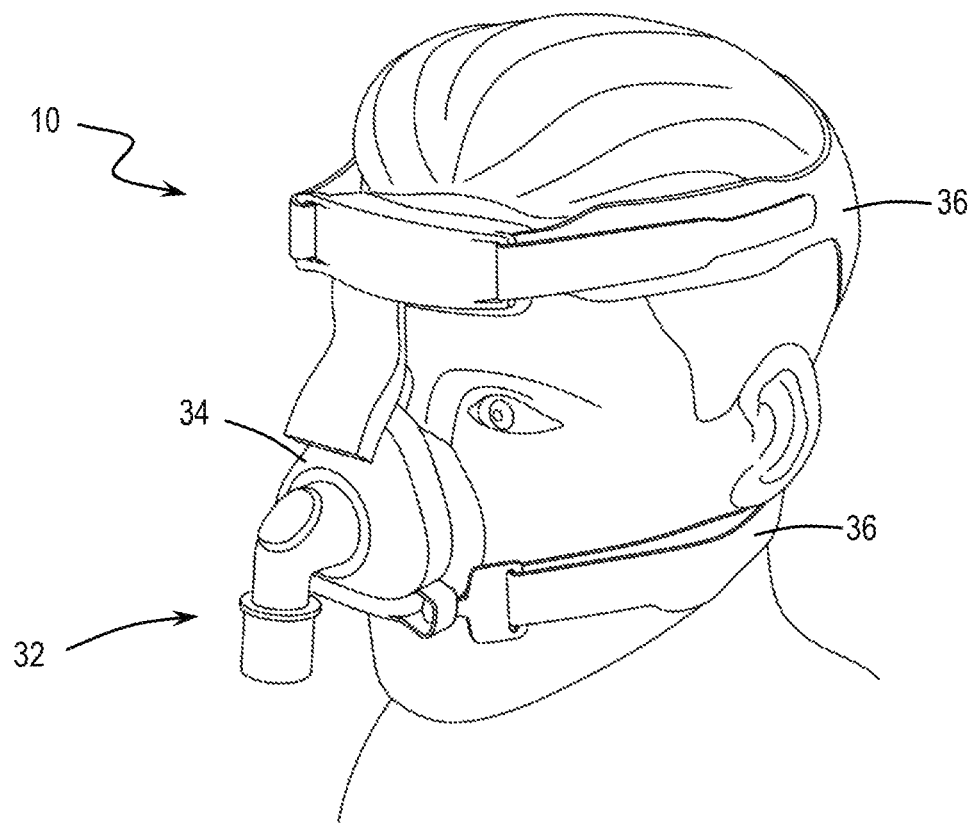
FIG. 4 is a perspective view of a nasal mask CPAP device in position on the face of a user.
Figure 5:
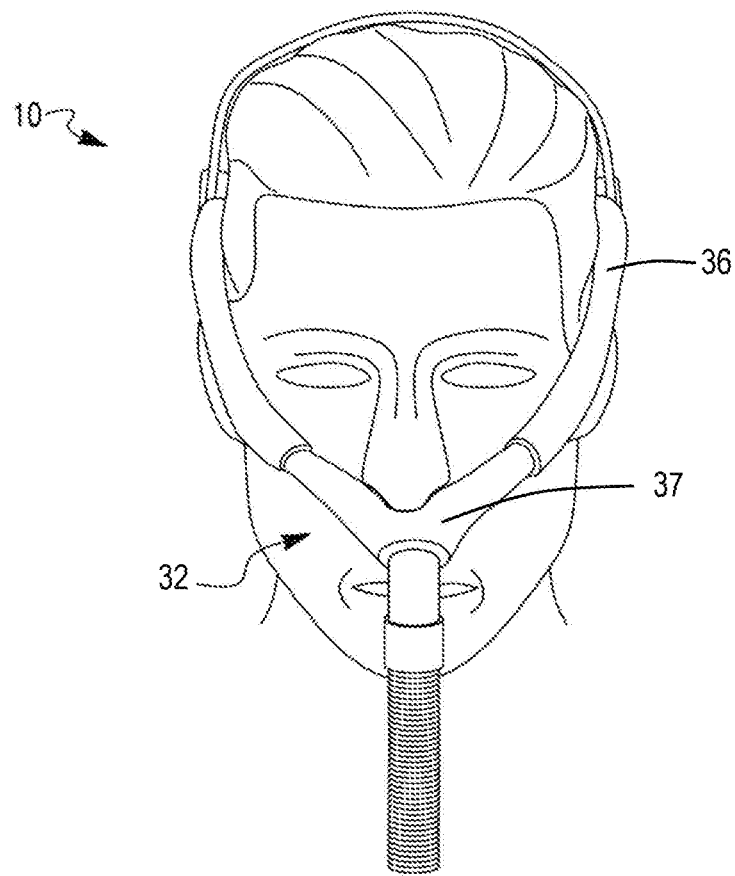
FIG. 5 is a front view of a nasal pillow CPAP device in position on the face of a user.
Figure 6:
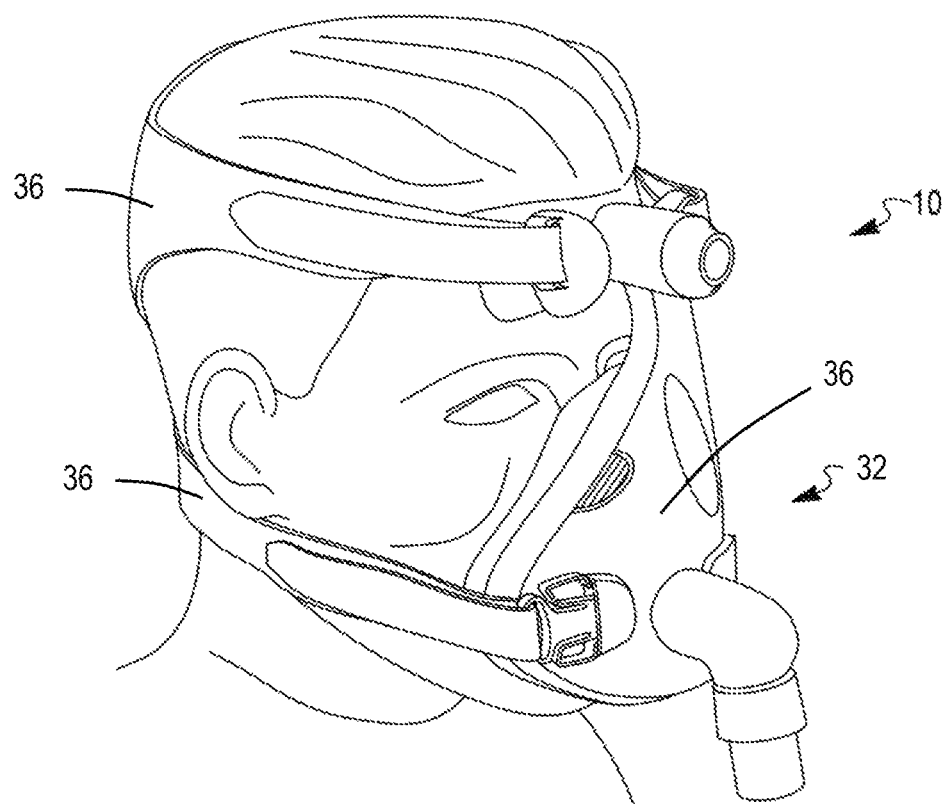
FIG. 6 is a perspective view of a full face mask CPAP device in position on the face of a user.

Referring now to FIGS. 4-6, a CPAP device 32 is shown continuously blowing pressurized air into nasal passage 20 of a user 10 to ensure that an airway 14 does not collapse (i.e., restrict) or close. Depending on the degree of airway collapsibility for a particular patient, a CPAP device 32 may deliver varying amounts of pressurized air. For example, a patient 10 (i.e., a user) with a relatively severe airway collapsibility will have a higher pressurization than does a patient having a relatively low airway collapsibility. The amount of pressurized air is titrated during a polysomnography ("PSG") until the airway 14 remains patent, that is, open and unobstructed.

There are three different approaches to a CPAP device 32. First, a nasal mask 34 may be used as shown in FIG. 4, which covers the nose only, surrounding the nostrils 18. The nasal mask 34 has a cross-section having an approximately triangular shape and has a silicone cushion. The nasal mask 34 is desirable for high-pressure air delivery, but it is ineffective for mouth breathers or those with temperature-induced allergies. Of the three approaches, the nasal mask 34 is the most popular option for a CPAP device 32. A nasal mask CPAP device 32 is shown in FIG. 4. As discussed above, straps 36 extend from the nasal mask 34 and around the user's 10 head in order to hold the nasal mask 34 securely in place on the user's face, even if the force from the nasal mask 34 and/or the straps 36 is uncomfortable.

In a second approach to a CPAP device 32, shown in FIG. 5, a nasal pillow 37, which is a plastic insert configured to fit directly into nostrils 18, may be used. The nasal pillow 37 creates an optimal seal in the nostrils 18, so it is desirable for relatively lower pressure delivery. However, the nasal pillow 37 is ineffective for users who naturally rely on predominantly oral respiration while sleeping (e.g., are mouth breathers) and may cause extreme nose dryness and/or pressure ulcers.

Third, as shown in FIG. 6, a full face mask 38 may be used. The full face mask 38 is currently the best option for mouth breathers. The full face mask covers approximately an entire portion of the face of a user 18, including both the user's lips 22 and the user's nostrils 18. However, the full face mask 38 restricts movement and requires significantly higher air-pressure levels than either the nasal mask 36 or the nasal pillow 37 in order to operate effectively in maintaining desirable breathing patterns in the user 10 during sleep. Further, the discomfort and difficulty of using a full face mask 38 result in a low compliance rate for patients regularly using the full face mask 38.

When a user is using a CPAP device 32, the user is aware when the CPAP device 32 is not keeping the user's airway 14 patent because leakage of air from nostrils 18 or the mouth 12 of the user 10 tends to wake the user 10. Specifically, when using the nasal mask 36, opening the mouth 12 causes pressurized air to enter the nostrils 18 and the nasal passage 20 and exit the mouth 12 of the user. A noticeable turbulence in the mouth cavity 16 will wake the user and cause the user to close the mouth 12 to continue receiving the pressurized air in the airway 14. Alternatively, the user 10 may remove the nasal mask 36 entirely, rendering treatment by a CPAP device 32 moot.

Figure 7:
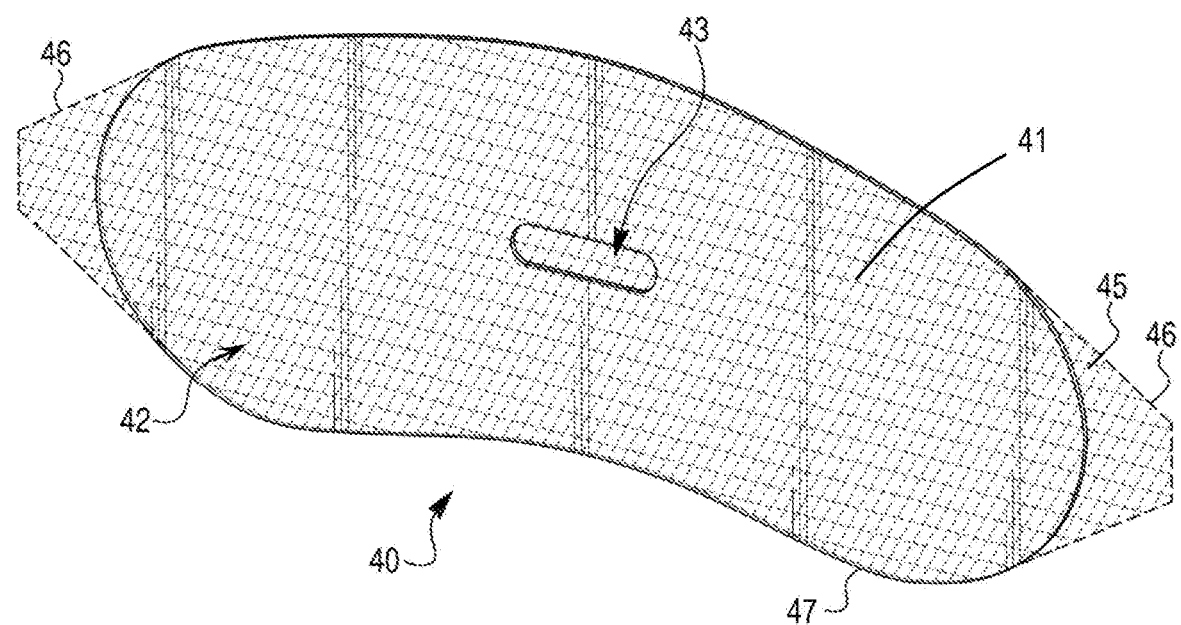
FIG. 7 is a front perspective view of a face strip according to an exemplary embodiment.
Figure 8:
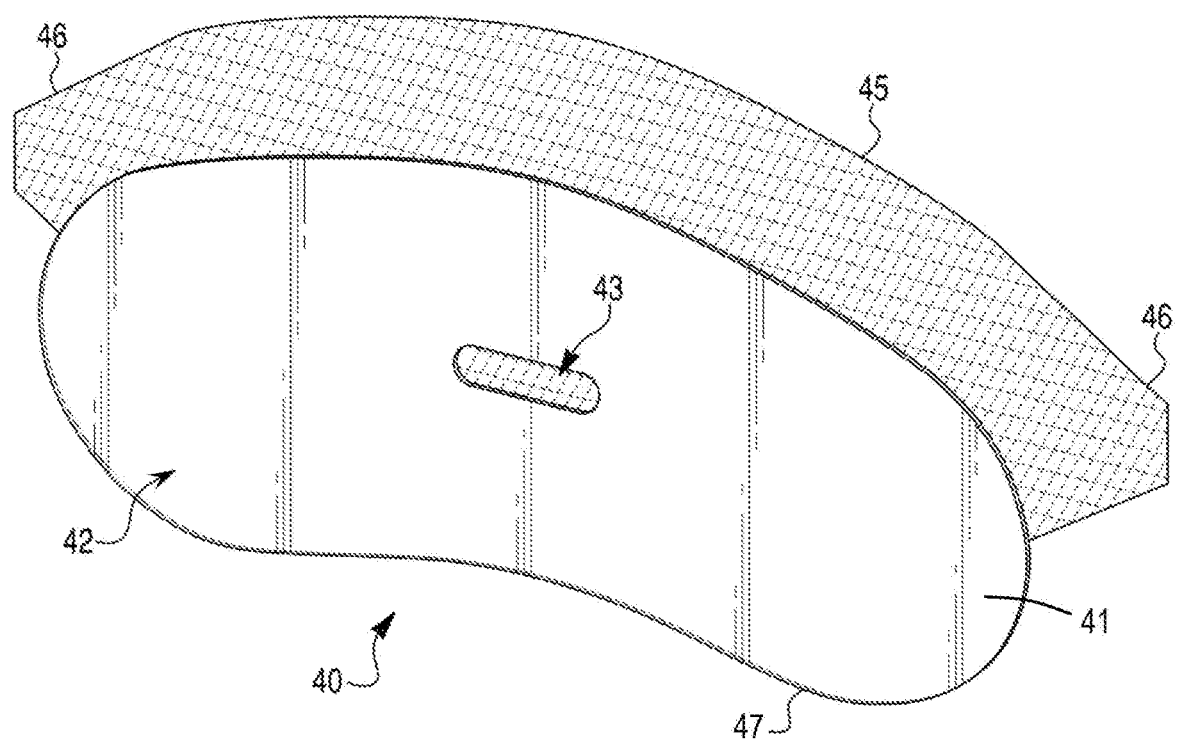
FIG. 8 is an exploded assembly view of a front side of the face strip shown in FIG. 7.
Figure 9:
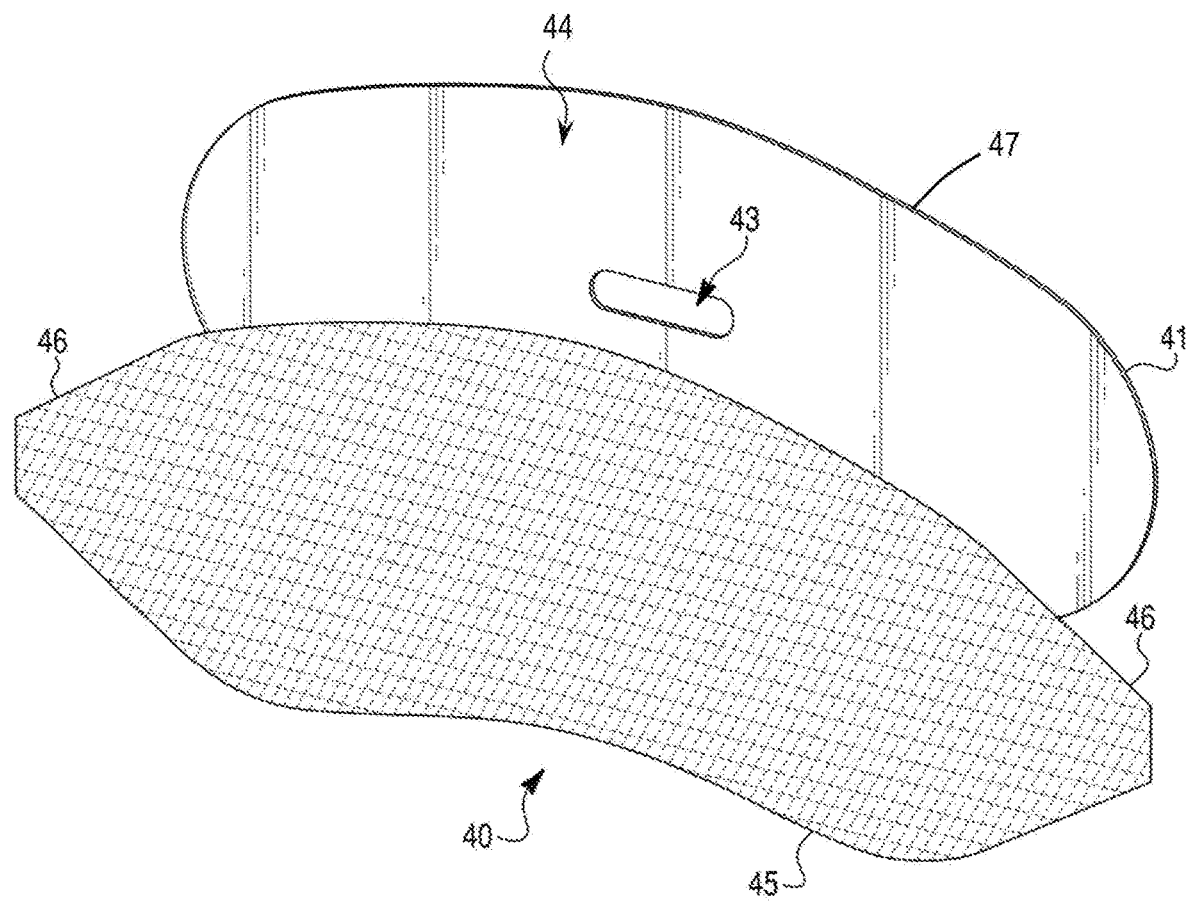
FIG. 9 is an exploded assembly view of a rear side of the face strip shown in FIG. 7.

Referring now to FIGS. 7-9 various views views of a face strip 40 (i.e., sleep strip, facial strip, breathing strip, etc.) are shown according to an exemplary embodiment. The face strip 40 includes an adhesive layer 41 having a front (i.e., first, forward, contact, engagement, etc.) surface 42 and an opposing rear (i.e., second, rearward, etc.) surface 44

(shown in FIG. 9). The face strip 40 may be formed of a flexible material, such that the face strip 40 has an elastic response when a mechanical force or stress is applied to and then subsequently released (i.e., removed) from the adhesive layer. In other words, when the force is removed, the mesh layer returns (i.e., rebounds) to its original shape and/or orientation. Further, the face strip 40 is configured to bend and conform to the user's face, such that the outer periphery 47 follows the curvature of the user's face when the face strip 40 is applied thereto. The adhesive layer 41 of the face strip 40 is configured to ensure that a user's lips are held in position such that the lips do not separate when the user is wearing the face strip 40.

The front surface 42 of the adhesive layer 41 is configured to adhere to a face of a user. An outer periphery 47 of the adhesive layer 41 corresponds to a shape of an outline of the user's lips and, when applied to the user's lips, holds the lips together in a generally closed position. In this configuration, the face strip 40 is configured to be securably attachable to (e.g., proximate, over, around, etc.) the user's mouth. According to one exemplary embodiment, the face strip 40 is configured to be securably attachable to at least a portion of the lips of a user, such as the vermillion of the upper lip or the vermillion of the lower lip of the user. According to another exemplary embodiment, the face strip 40 is configured to be securably attachable only to an external portion of the lips or mouth of the user. According to yet another exemplary embodiment, the face strip 40 is configured to be securably attachable to an internal portion and/or an external portion of the lips or mouth of the user. According to other exemplary embodiments, the face strip 40 is configured to be securably attachable over, under, and/or around the upper lip and the lower lip of the user. For example, the face strip 40 may be configured to be securably attachable both to the upper lip and the lower lip of the user and to a region of the face of the user extending to approximately 2 mm beyond the edges of the upper lip and the lower lip of the user. To the extent that this application describes securably attaching the face strip 40 to various portions of the user's face, it is referring to a portion of the front surface 42 of the adhesive layer 41. It should be understood that this portion may refer to the outer periphery 47 of the adhesive layer 41 or may refer to other portions of the front surface 42.

It should be understood that the adhesive layer 41 of the face strip 40 may adhere to different users having mouths with different shapes and sizes at different points of the lips and/or face. In this configuration, the face strip 40 has a "one-size-fits-all" shape and size, such selected to adhere to the faces of most users. However, while FIGS. 7-9 show the face strip 40 with one size and a single shape of the outer periphery 47, it should be understood that according to other exemplary embodiments, face strips 40 having different shapes and/or sizes (e.g., larger sizes) of the outer periphery 47 may be provided to accommodate users with larger or irregularly shaped or sized mouths or other facial features (e.g., cleft lip) or abnormalities.

When the face strip 40 is applied to the user's lips or face, the face strip 40 holds the user's lips in a closed position relative to one another. However, unlike a MAD, the face strip 40, particularly due to its flexibility and because it does not engage the user's teeth, does not place an external stress on the user's mouth or jaw. As a result, the user's jaw is able to be positioned comfortably in its natural resting position when the face strip 40 is applied and the user's lips are in the closed position. Even as the user's jaw moves around, the adhesive layer 41 maintains its adhesive contact with the user's lips or face to hold the lips together in the closed position.

Figure 10:
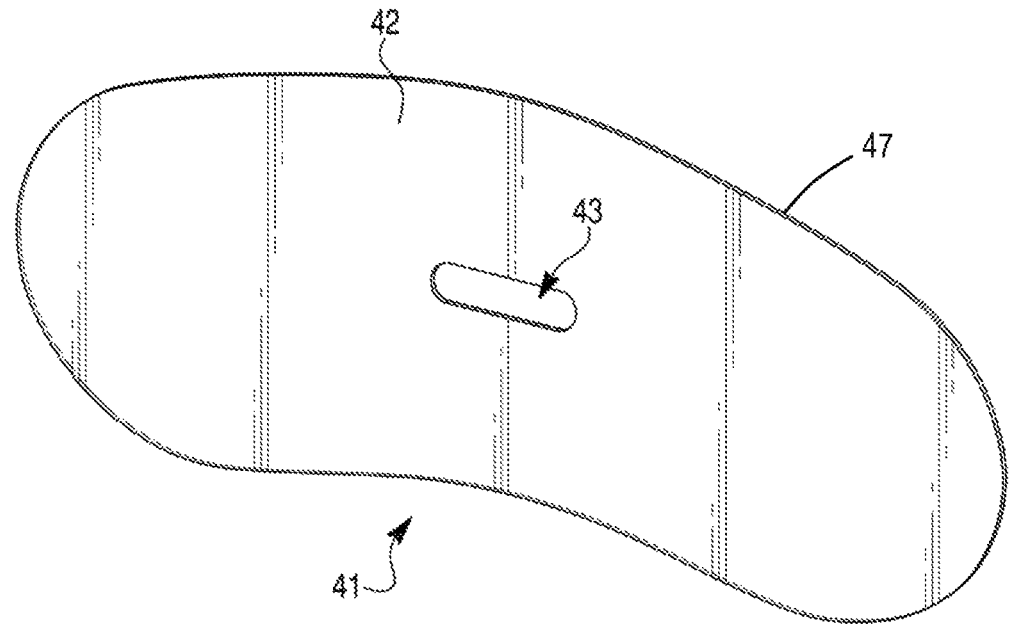
FIG. 10 is a perspective view of a front surface of the face strip according to one aspect.

The front surface 42 of the adhesive layer 41 is equipped with an adhesive substance, which is sufficiently strong to bind the face strip 40 temporarily to skin, yet preferably does not irritate the skin or leave a sticky residue on the skin. According to an exemplary embodiment, one or both of the adhesive layer 41 and the adhesive may be formed from a Silicone-based or other hypoallergenic material to ensure that use of the face strip 40 does not cause a reaction to a user when applied to his or her face and/or lips. Referring to FIG. 10, the front surface 42 of the adhesive layer 41 is shown according to an exemplary embodiment. In this configuration, the adhesive covers substantially the entire surface of front surface 42, such that any portion of the front surface 42 may be adhesively coupled to the user's lips or face.

Figure 11:
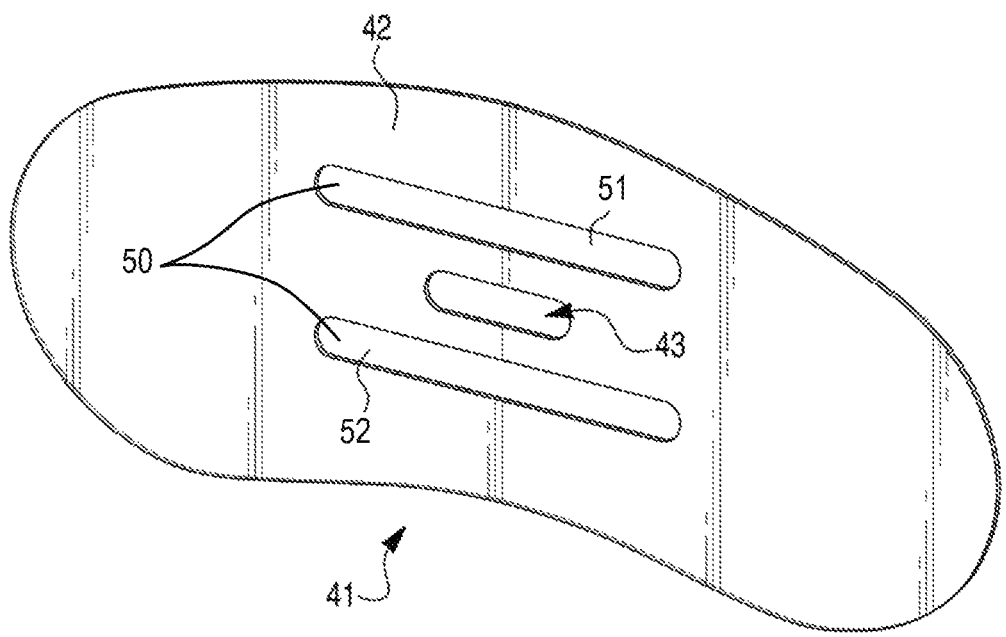
FIG. 11 is a perspective view of a rear surface of the face strip according to another aspect.

Referring now to FIG. 11, the front surface 42 of the adhesive layer 41 is shown according to another exemplary embodiment. In this configuration, the adhesive covers a portion of the front surface 42 of the adhesive layer 41, which is less than the entire front surface 42. For example, the adhesive layer 41 includes at least one adhesive strip 50 (e.g., a plurality of adhesive strips 50) disposed on the adhesive layer 41, while the rest of the front surface 42 of the adhesive layer may not adhere to the user's lips or face. As shown in FIG. 11, the at least one adhesive strip 50 includes a first adhesive strip 51 and a second adhesive strip 52. The first adhesive strip 51 may be configured to be securably attached to the user's upper lip and the second adhesive strip 52 may be configured to be securably attached to the user's lower lip, although it should be understood that the first and second adhesive strips 52 may be securably attached to the user's lips or face in other ways or locations.

While FIG. 11 shows the adhesive layer 41 having two adhesive strips 50, it should further be understood that the adhesive layer 41 may include more or fewer adhesive strips 50. Furthermore, the first and second adhesive strips 51, 52 may have any suitable shape. For example, the shapes of the adhesive strips 50 may correspond to shapes of a user's lips or may have other shapes (e.g., parallel strips, arcuate, etc.). The adhesive substance is preferably clear, although it is further contemplated that the adhesive may have a slight coloration to it, in order to help the user easily differentiate between the rear surface 44, which may not have the adhesive applied thereto, and the front surface 42 of the adhesive layer 41, which would be colored by the adhesive.

According to an exemplary embodiment, the adhesive is substantially water-resistant. For example, in the event that the user begins to sweat, the sweat does not permeate into the adhesive or affect the adhesiveness of the adhesive. As a result, the adhesive layer 41 remains securely attached to the user's lips or face, as sweat forms around the adhesive layer 41. Similarly, as saliva forms in the user's mouth or moisture from the user's breath engages the adhesive proximate the user's lips, the saliva or moisture does not disturb the adhesive, allowing the adhesive layer 41 to remain securely attached to the user, even if the user's lips separate from the closed position toward an open position.

According to another exemplary embodiment, the adhesive and/or the adhesive layer 41 is preferably non-toxic. The non-toxicity of the adhesive is critical as the adhesive is preferably positioned, such that it comes into close contact with the user's lips, mouth, and/or face. The adhesive is intended to affix the present invention to the upper lip and lower lip and/or the jaw of the user. For example, the adhesive is configured to be releasably secured only onto the user's lips. When the user is finished using the face strip 40, the user may separate the adhesive layer 41, including the adhesive, from the user's lips or face, removing the face strip 40 therefrom.

According to an exemplary embodiment, the adhesive is preferably covered with an adhesive backing, such as a piece of waxed paper, in order to keep the adhesive layer 41 clean and, preferably, sterile until the adhesive backing is removed for application of the face strip 40 to the user's mouth. Specifically, the user removes at least a portion or all of the adhesive backing, aligns the adhesive with his or her lips and/or face, and presses the face strip 40 firmly against the user's mouth until the adhesive securably attaches the adhesive layer 41 directly to the user's mouth. According to an exemplary embodiment, the user may remove the face strip 40 from his or her face. When the face strip 40 is removed, substantially all of the adhesive remains adhered to the adhesive layer 41. In this configuration, the adhesive is also configured to leave little to no sticky residue behind, and is capable of holding a stable position on the face of the user that endures for the duration of a sleep or exercise session. After the face strip 40 is removed, the face strip 40 may be either discarded, or the adhesive backing may be reapplied to the adhesive layer 40 to protect the adhesive and protects its adhesive properties by preventing the adhesive from drying out. The adhesive backing may subsequently be removed again and the adhesive layer 41 may be reapplied to the user's mouth for subsequent uses of the face strip 40.

Referring still to FIGS. 7-9, the rear surface 44 of the adhesive layer 41 is configured to adhere to a mesh layer 45 and is securely fixed (i.e., attached, coupled, etc.) to the mesh layer 45. In the face strip 40, the adhesive layer 41 and the mesh layer 45 cooperate and are configured to ensure that a user does not rely fully upon oral respiration during sleep, as oral respiration predisposes the user to snoring and/or apnea, as well as dry mouth, or to control the flow of air through the user's mouth during exercise activity.

The mesh layer 45 is formed of a paper-thin cloth, a silicone sheet, a woven paper, or similar soft material. Preferably, the mesh layer 45 is formed of polyester. The mesh layer 45 is disposed in contact with rear surface 44 of adhesive layer 41. The mesh layer 45 is configured to be stretchable, yet strong enough to not break or puncture when stretched.

According to an exemplary embodiment, the mesh layer 45 includes at least one (e.g., a plurality of) release tab 46 extending laterally outward from the outer periphery 47 of the adhesive layer 41. For example, the at least one release tab 46 is preferably positioned on a left and/or a right side of the mesh layer 45, and is aligned approximately with where the upper and lower lips intersect when the face strip 40 is applied to the user's mouth. According to an exemplary embodiment, the adhesive layer 41 securably attaches to the user's lips and the release tabs 46 overlap with the user's face and/or vermillion. Because the release tabs 46 extend beyond the adhesive layer 41, the release tabs 46 are free from adhesive and do not adhere to the user's face or lips. In this configuration, the at least one release tab 46 is configured to facilitate the removal of the face strip 40 from the user's lips or face when the user is finished using the face strip 40. To use the at least one release tab 46, the user lifts the release tab 46 away from the user's face, pinching and gripping the release tab 46, and pulling the release tab 46 away from the face (e.g., approximately orthogonally). The release tab 46 allows for the user to peel the face strip 40 off quickly and easily. Further, by pulling the release tab 46 in this direction, the release tab 46 facilitates separation of the adhesive from the user's lips or mouth and prevents the adhesive from leaving residue on the user's mouth.

It should be understood that the face strip 40 is capable of remaining securely affixed to or over and/or under the lips and jaws of the user for the duration of a sleep or exercise session due to the strength and rigidity of the material used to form the mesh layer 45, as well as due to the efficacy of the adhesive layer 41 of the face strip 40. For example, the face strip 40 is configured to be securably attachable to an external portion of the lips of the user. It should further be understood that the adhesive layer 41 and/or the mesh layer 45 are preferably hypoallergenic and kept in a sterile container (i.e., pouch, package, etc.) until use. For example, the face strip 40 may also be kept in a sterile, preferably polypropylene envelope, in order to ensure that dirt and other contaminants do not compromise the sterility of the face strip 40.

Referring to FIGS. 7-10, the adhesive layer 41 has at least one opening 43 (i.e., permeation, hole, orifice, etc.) extending therethrough, from the front surface 42 to the opposing rear surface 44. The opening 43 is configured to allow air to pass through the face strip 40. The opening 43 is positioned on the face strip 40 in a configuration, such that when the face strip is worn by the user, the opening 43 is disposed proximate and/or between the user's lips and exposed to the user's mouth cavity, allowing oral respiration therethrough. According to an exemplary embodiment, the at least one opening 43 is positioned at a central position on the adhesive layer 41, although one or more openings 43 may be positioned at other portions of the adhesive layer 41 according to other exemplary embodiments.

It should be understood that according to an exemplary embodiment, before the adhesive layer 41 is applied to a user's lips, the user spaces his or her lips apart slightly, with the jaw in a relaxed position. The face strip 40 is then aligned with the user's mouth, such that the opening 43 is disposed between the user's upper and lower lips. According to another exemplary embodiment, before the adhesive layer 41 is applied to the user's lips, the user presses his or her lips together to a completely closed position. The face strip 40 is then aligned with the user's mouth, such that the opening 43 is disposed over and aligned with a location where the user's lips touch. In this configuration, at least a portion of the opening 43 may be disposed over each of the user's upper and lower lips. The face strip 40 then secures the lips in a closed position, further restricting airflow out of the user's mouth. In the event that nasal respiration is too restrictive to breathe properly, the user may either forcibly separate his or her lips, while maintaining at least some adhesive contact between the adhesive layer 41 and the lips, allowing oral respiration through the opening 43. Similarly, the user may lower the jaw, forcing the lips apart slightly, and exposing the opening 43 to the user's mouth, while maintaining adhesive contact between the user's lips and the adhesive layer 41.

According to an exemplary embodiment, the adhesive may be applied directly to substantially the entire front surface 42 of the adhesive layer 41, such that any portion of the front surface 42 may be applied to the user's lips or face for securably attaching the face strip 40 thereto. According to another exemplary embodiment, the adhesive may be applied to only a portion of the front surface 42. The adhesive may be applied at a height directly above and/or below the at least one opening 43. For example, the adhesive may be applied in this configuration as adhesive strips 50 (as described above with respect to FIG. 11) or may applied directly to the adhesive layer 41 in different ways or at different locations. According to another exemplary embodiment, the face strip 40 may be sized and configured for users having smaller mouths or faces, such that the adhesive is disposed on the adhesive layer 41 at a position surrounding and/or coming into direct contact with the at least one opening 43 or may be applied proximate and come very near to the site of the at least one opening 43 of face strip 40. In this configuration, even if the user's lips are similar in size but larger than the opening 43, the face strip 40 may still be securably attached directly to the user's lips.

The mesh layer 45 may cover substantially the entire rear surface 44 of the adhesive layer 41. For example, the mesh layer 45 may overlay the at least one opening 43, such that when the user engages in oral respiration, the user breathes through the at least one opening 43 and directly through the mesh layer 45. In this configuration, the adhesive layer 41 is substantially non-porous, directing all air through the at least one opening 43. The mesh layer 45 may be porous and configured to allow air to pass from the at least one opening 43 in the adhesive layer 41 through the material of the mesh layer 45, even without a corresponding opening formed in the mesh layer 45. Notably, the mesh layer may provide additional resistance that, together with the area of the opening 43, restrict airflow during oral respiration. Because the at least one opening 43 is covered by mesh layer 45, the face strip 40 is configured to provide a constricted, alternate passage for air in the event that the user's nasal passage becomes clogged, and alternate breathing through the mouth is required.

According to another exemplary embodiment, the mesh layer 45 only covers the opening 43 and does not cover the rest of the adhesive layer 41. According to yet another exemplary embodiment, the mesh layer 45 defines at least one opening (not shown) extending therethrough and corresponding to the at least one opening 43 in the adhesive layer 41, such that the at least one opening 43 in the adhesive layer 41 is exposed directly to an external environment and such that when the user engages in oral respiration, the user breathes through the at least one opening 43 in the adhesive layer 41 without also breathing through the material forming the mesh layer 45. In this configuration, the mesh layer 45 provides a surface for the user to interact with (e.g., with release tabs 46), but does not affect the resistance generated by the opening 43 in the adhesive layer.

Entry and exit points of a nasal cavity (i.e., the two nostrils) generally have a total area of approximately 350 square millimeters. However, humans generally use only one nostril when breathing nasally (e.g., approximately 175 square millimeters). The relatively small size of the two nostrils assists in optimizing a $CO_2$—$O_2$ exchange, as air is recycled, allowing more time to extract maximum 02. On the other hand, the entry and exit point of the oral cavity (i.e., the mouth) is significantly larger. When a person breathes orally, the person may exacerbate airway collapse by exhaling all of the air in the respiratory airway upon exhalation. Oral respiration reduces the amount of time that air is retained in the user's lungs and therefore decreases the amount of $O_2$ retained when compared to nasal respiration. Such loss of $O_2$ may additionally contribute to hypoxia. As a result, in order to maximize $O_2$ consumption, it is advantageous to promote nasal respiration. Oral respiration reduces the amount of time that air is retained in the user's lungs and therefore decreases the amount of $CO_2$ in the blood when compared to nasal respiration. The reduced state of $CO_2$ may additionally contribute to hypoxia due to worsened $O_2$ delivery. As a result, in order to optimize blood oxygenation, it would be advantageous to promote nasal respiration.

The opening 43 is purposely small to encourage nasal breathing. However, the at least one opening 43 allows for oral respiration if nasal breathing becomes impossible. The opening 43 was designed after carefully considering the average human nostril area, nasal cavity, and oral cavity. The at least one opening 43 may mimic the nostrils, with mesh layer 45 acting as a filter, and the small size of the opening 43 acts as a check valve to preclude or slow full oral exhalation, thereby extending the duration of and improving $CO_2$—$O_2$ exchange in the lungs. Further, in the event of full nasal blockage and difficulty with oral respiration, a user may remove the face strip 40 without using his or her hands by forcibly separating his or her lips by lowering the jaw away from the upper palate. This removal ability reduces or prevents the possibility of hypercapnia, which occurs when there are excessive levels of $CO_2$ in the blood if nasal respiration becomes too restrictive.

The at least one opening 43 exists to provide a restricted channel for air to pass through. The at least one opening 43 is preferably small, having an area about or less than 125 square millimeters according to an exemplary embodiment. In this or other configurations, the area of the at least one opening 43 is less than an area of one or two average nostrils. According to an exemplary embodiment, the dimensions of the at least one opening 43 extending in a lateral orientation (e.g., as shown in FIGS. 7-9) include a height of between approximately 2.5 and 5.0 millimeters and a width of between approximately 12.5 and 19.0 millimeters. According to another exemplary embodiment, the at least one opening 43 has a height of approximately 3.2 millimeters and a width of approximately 15.9 millimeters. According to another exemplary embodiment, the at least one opening 43 has an area of approximately 100 square millimeters, although according to other exemplary embodiments, the at least one opening 43 has an area of about 50 square millimeters. It should be understood that when the at least one opening 43 includes a plurality of openings 43, the total (i.e., cumulative) area of all of the openings 43 may have the areas described above.

Alternate embodiments of the present invention may include variations on the size of the at least one opening 43. For example, for users with a large lung capacity, the standard size of the opening 43 of the present invention may be too small, which could cause an individual to faint from a lack of oxygen if his or her nasal passages become blocked during the use of the present invention. As such, some versions of the face strip 40 may be equipped with an opening 43 that has a larger area or diameter, or if the opening 43 includes a mesh layer 45 overlaying the opening 43, the mesh layer 45 may be more porous (e.g., less fine) or equipped with additional small holes to permit slightly greater air flow therethrough.

It should be understood that the at least one opening 43 may be configured with the desired area in various suitable geometries. For example, the at least one opening 43 may have a square shape, a rectangular shape, or a circular shape, among other shapes. According to another exemplary embodiment, as shown in FIGS. 7-9, the at least one opening has an elongated elliptical shape. It should further be understood that when the at least one opening 43 includes a plurality of openings 43, each of the openings 43 may have the same or different shapes.

During use of the face strip 40, the opening 43 is configured to limit or prevent a user from oral respiration.

The quantity and/or area of the opening or openings 43 is provided to limit the user from subconsciously breathe through the mouth. The smaller area of the opening 43 relative to the user's mouth restricts airflow through the opening 43 relative to a user's typical oral respiration air flow. Under Bernoulli's principle, as the area of the opening 43 decreases, the pressure at the opening 43 increases, causing resistance to oral respiration and forcing the user to inhale and exhale through nasal respiration in addition to or instead of oral respiration. Specifically, the opening 43 may have an area that is small enough to force the user to rely on nasal respiration. For example, a differential in a higher pressure buildup in the user's mouth (e.g., due to the resistance of the size of the opening 43) relative to the lower pressure flow through the user's nasal passage may apply a rearward force on the user's tongue, pressing the tongue into engagement with the upper palate of the user's mouth and sealing the user's mouth cavity. This pressure differential then may lead to complete nasal respiration unless restriction in the nasal passage builds up pressure in the nasal passage, causing a drop in the differential between the nasal passage and the mouth cavity and forcing oral respiration.

Figure 12:
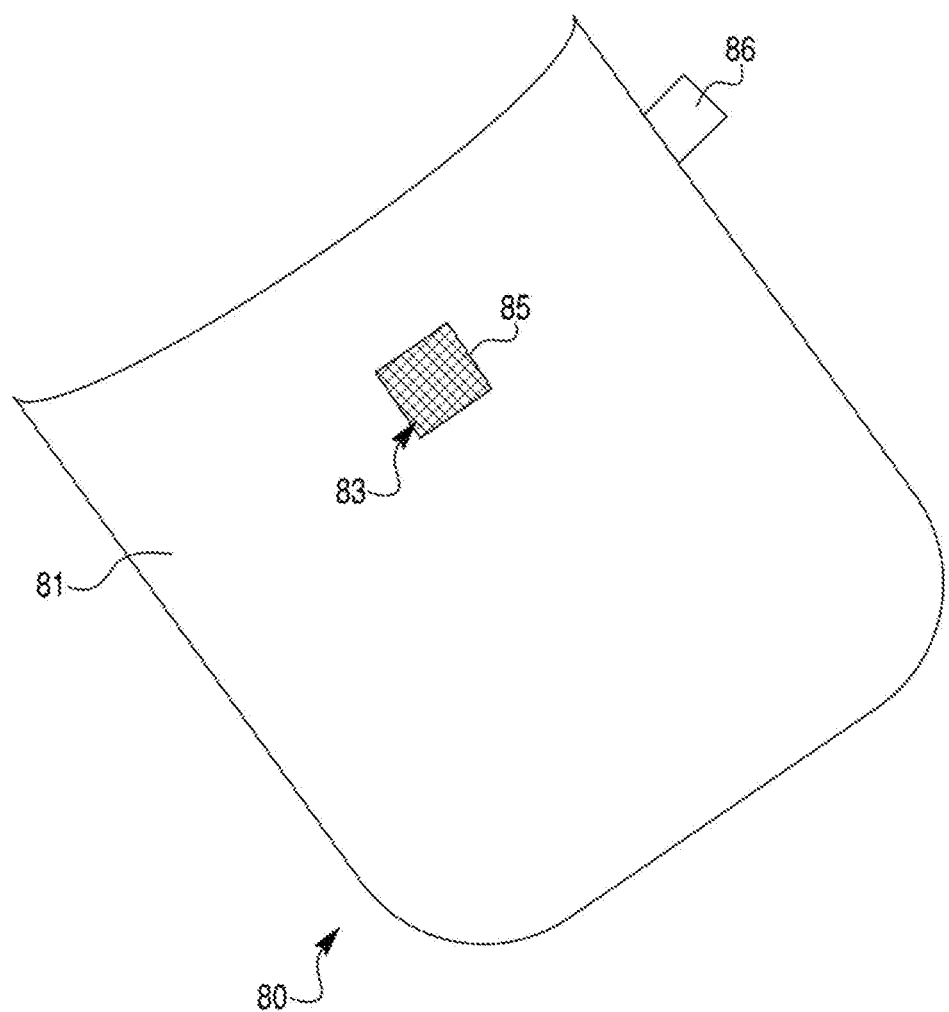
FIG. 12 is a front perspective view of a face strip according to an exemplary embodiment.

Referring now to FIG. 12, a face strip 80, which is substantially similar to the face strip 40, except as described below, is shown according to an exemplary embodiment. The face strip 80 includes an adhesive layer 81 substantially similar to the adhesive layer 41, having an opening 83 located in a middle (e.g., an upper middle) portion of the adhesive layer 81. The opening 83 has a substantially square cross-sectional shape. A mesh layer 85 substantially similar to the mesh layer 45 is disposed over and upon the opening 83, such that the mesh layer 85 does not extend beyond any edges of the opening 83 in the adhesive layer 81. The face strip 80 also includes a release tab 86 configured to facilitate the removal of the face strip 80 from the face of a user after the sleep or exercise session is completed.

Figure 13:
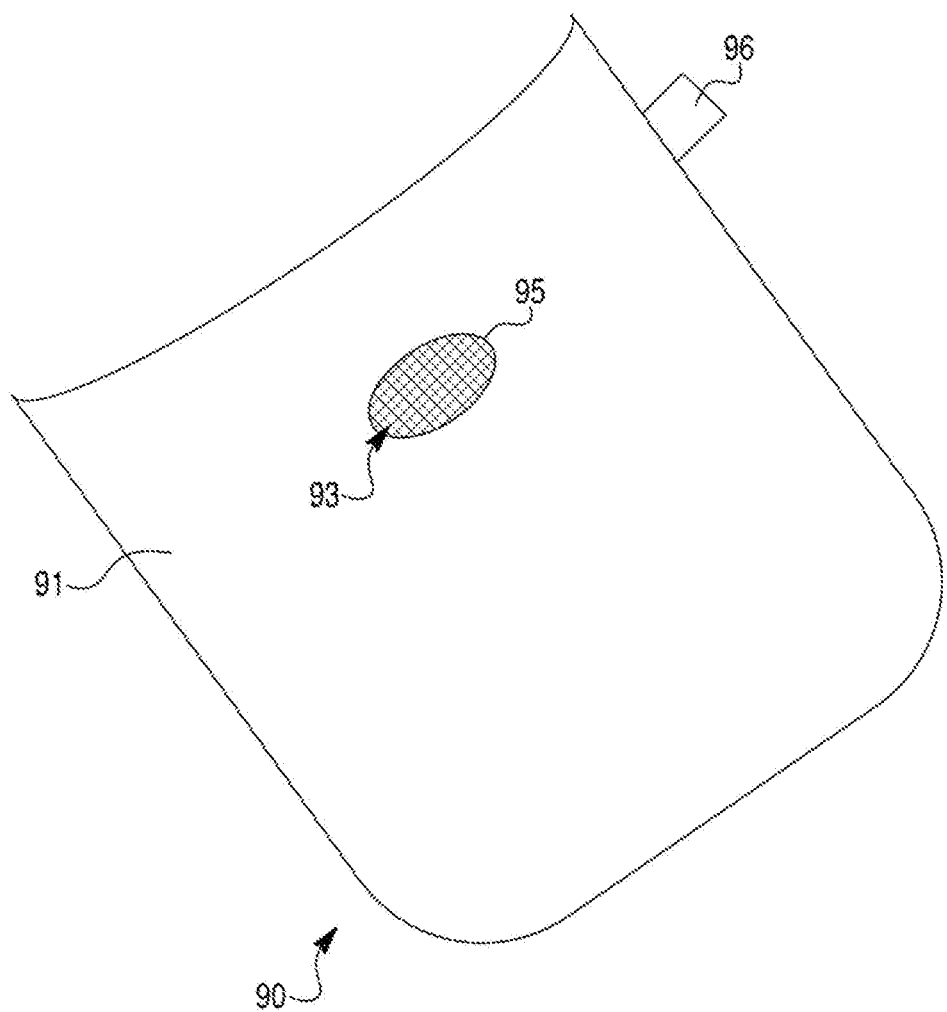
FIG. 13 is a front perspective view of a face strip according to another exemplary embodiment.

Referring now to FIG. 13, a face strip 90, which is substantially similar to the face strips 40, 90, except as described below, is shown according to an exemplary embodiment. The face strip 90 includes an adhesive layer 91 substantially similar to the adhesive layer 41, 81, having an opening 93 located in a middle (e.g., an upper middle) portion of the adhesive layer 91. The opening 93 has a substantially elliptical (e.g., circular) cross-sectional shape. A mesh layer 95 substantially similar to the mesh layers 45, 85 is disposed over and upon the opening 93, such that the mesh layer 95 does not extend beyond any edges of the opening 93 in the adhesive layer 91. The face strip 90 also includes a release tab 96 configured to facilitate the removal of the face strip 90 from the face of a user after the sleep or exercise session is completed.

In the event that the user has a full face beard, the adhesive may be less effective than when placed directly on a user without facial hair. It therefore is contemplated that in another exemplary embodiment, the face strip 40 may be equipped with at least one elastic band which may facilitate the stable placement of the face strip 40 on to the user's face. The elastic band is preferably affixed to the sides of the face strip 40 (e.g., at the release tabs 46 or other portion of the face strip proximate a lateral end), and is capable of retaining the face strip 40 in an approximately ideal location by securing the face strip 40 to the user's face with the elastic band around the user's ears and/or the back of his or her head. Notably, when the face strip 40 is applied in this fashion, the at least one opening 43 is approximately centered between the user's lips. According to an exemplary embodiment, the adhesive is preferably adhered to at least a portion of the user's lips or face, even if the efficacy of the adhesive over an extended period of time is diminished due to the presence of facial hair. According to another exemplary embodiment, a smaller face strip 40 may be provided, and configured to extend only over the user's lips and not beyond the user's vermillion to cover other portions of the user's face. In this configuration, the smaller face strip 40 interacts with and engages only the user's lips, ensure that no facial hair is not disposed between the adhesive and the user's lips.

Figure 14:
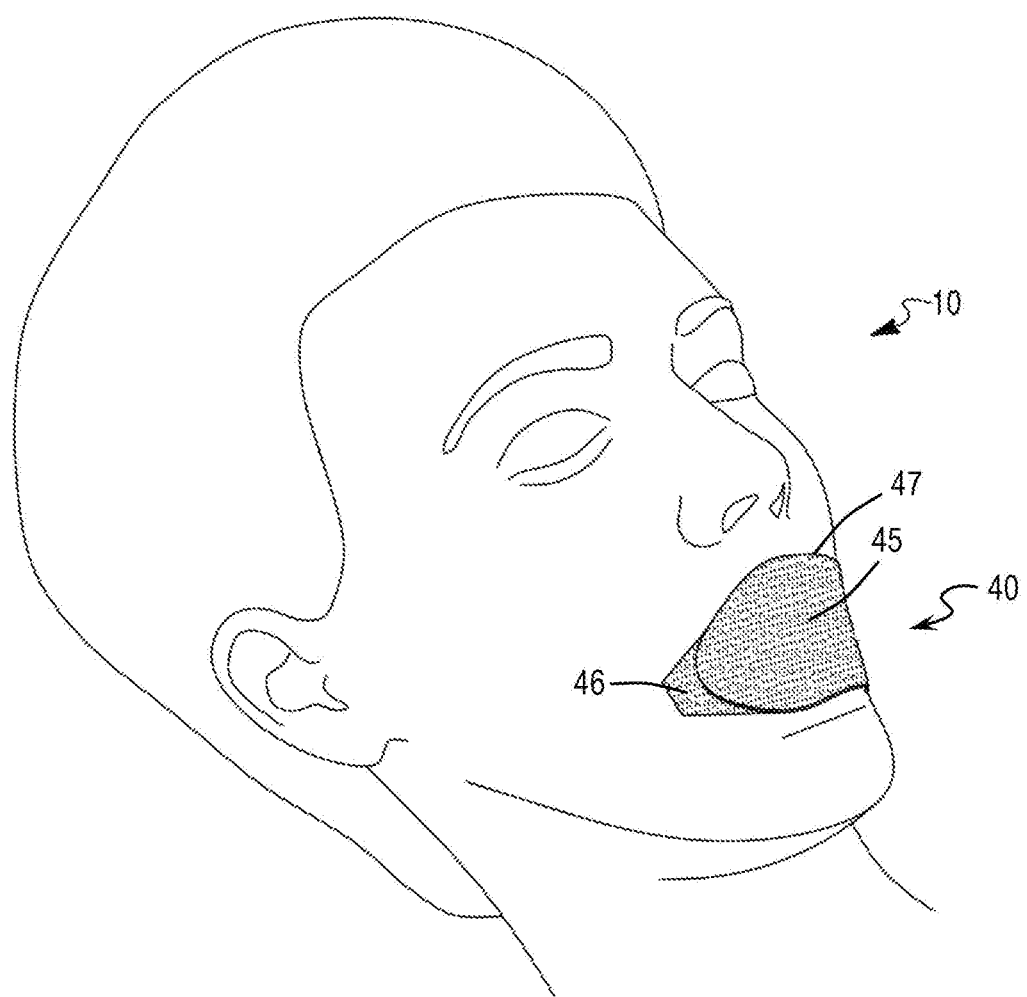
FIG. 14 is a perspective view of the face strip applied to the face of a user.

Referring now to FIG. 14, a user 10 is shown with the face strip 40 applied over his or her mouth for treatment of various breathing or other mouth-affected conditions. While the user 10 is shown sleeping, it should be understood that the face strip 40 may be used in both awake and sleeping applications to treat these various conditions. The face strip 40 may include any of the configurations discussed above.

Figure 15:
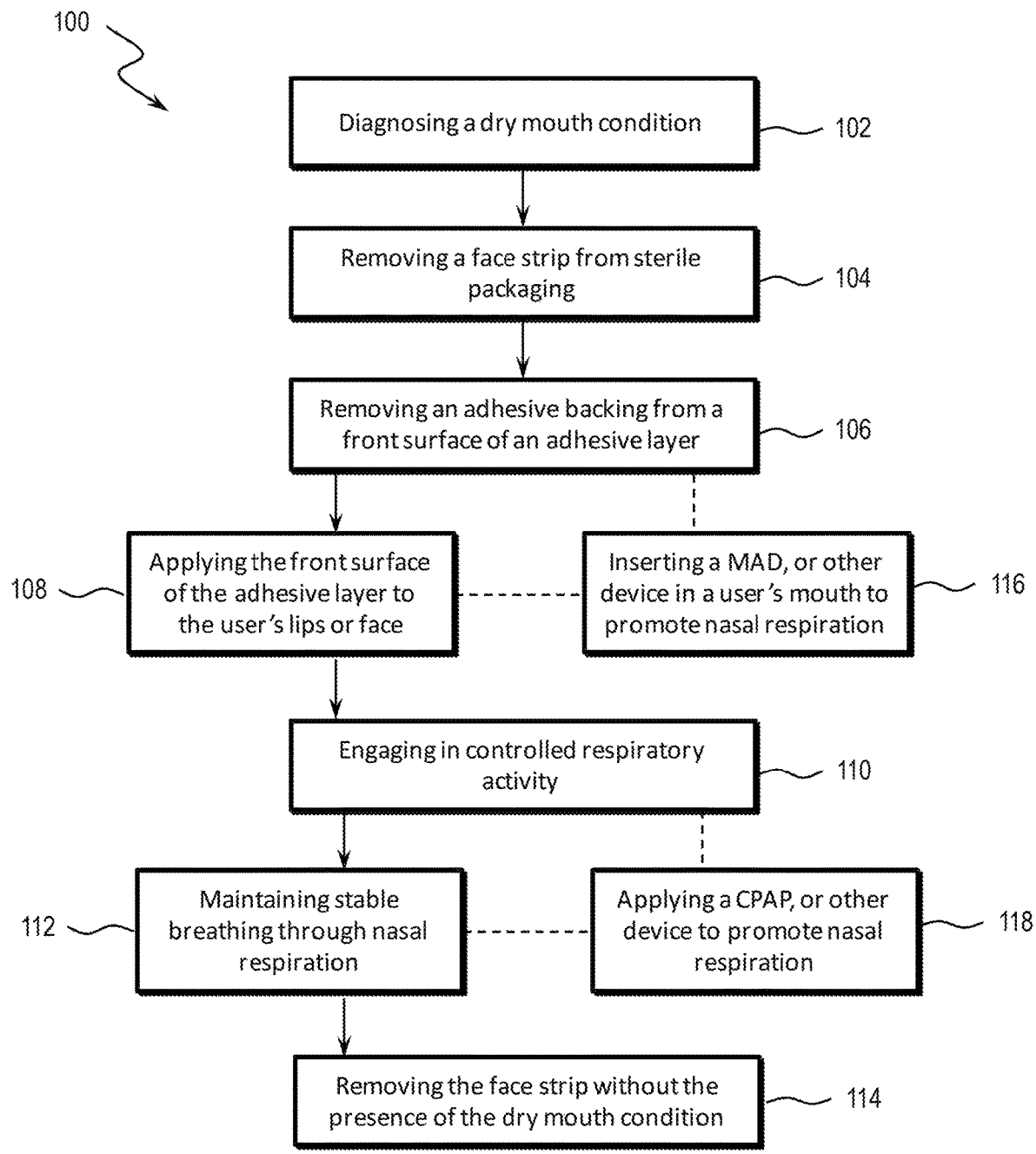
FIG. 15 shows a method of treating dry mouth in a patient using a face strip, according to an exemplary embodiment.

Referring now to FIGS. 15-18, methods for treating various breathing or other conditions are shown and described according to various exemplary embodiments. Referring first to FIG. 15, a method 100 of treating dry mouth (xerostomia) is shown according to an exemplary embodiment. In a dry mouth condition, the salivary glands in a patient's mouth do not produce a sufficient amount of saliva to keep the mouth wet and moist. Dry mouth may vary in intensity and duration and long-term persistence may ultimately lead to declining health of the patient's teeth and/or gums.

Dry mouth is commonly caused as a side effect of certain medications or medical treatments (e.g., user of a MAD or CPAP device for sleep apnea treatment), although factors such as nerve damage or paralysis, which limit control over the jaw muscles, as well as lifestyle choices (e.g., use of tobacco, alcohol, or psychoactive drugs), may also contribute to dry mouth. Further, dry mouth may develop due to long-term oral respiration (e.g., for approximately 1-8 hours consecutively or non-consecutively). When a patient breathes through an open mouth (e.g., when the patient is snoring), dry mouth occurs as moisture is exhaled from the open mouth. To remedy dry mouth caused by any of these situations, limiting or preventing oral respiration by maintaining the mouth in a closed position will help retain moisture in the mouth, preventing dry mouth from developing. Specifically, by inhibiting oral respiration, a user engages in primarily or exclusively nasal respiration, bypassing the mouth and further retaining moisture therein.

The method 100 includes a first step 102, including diagnosing a dry mouth condition, caused by a blockage and/or restriction in at least one of a patient's airways. Dry mouth is often difficult to diagnose because the underlying symptoms are often initially difficult to detect. Further, patients suffering from dry mouth are typically unaware of their oral respiration patterns, which only occurs while the patient is sleeping, although the patient may experience the effects of dry mouth throughout the day, while they are awake.

In the first step 102, a process of diagnosing a patient suffering from dry mouth may be performed by a polysomnography (e.g., a monitored overnight sleep session at a sleep center). Dry mouth may be identified when a patient's mouth falls open during deep sleep and/or rapid eye movement ("REM") sleep, due to relaxation of the jaw muscles when the person enters into one of these sleep states. This diagnosis may be made by observing, during polysomnography or at other times, the patient's mouth position while sleeping. Once the patient's mouth opens, the patient engages in primarily or exclusively oral respiration, rather than nasal respiration, as occurs when the patient's mouth is in a closed position.

A diagnosis of dry mouth may further be performed by identifying at least one symptom of extended oral respiration. For example, symptoms of dry mouth may include one or more of a sticky, dry feeling in the mouth or throat; frequent or excessive thirst during the sleep session or when the patient wakes up; oral sores; a burning or tingling feeling in the mouth (e.g., on the tongue); a dry, red, or raw tongue; difficulties speaking, tasting, swallowing, and/or chewing; voice hoarseness; dry nasal passages; sore throat; and/or bad breath. The presence of one or more of these symptoms may be in addition to or in place of visual observations of oral respiration during a sleep session. It should be understood that such symptoms may affect patients, regardless of age or sex. Further, the diagnosis of dry mouth may be made even if the patient does not have or show signs of sleep apnea or snoring. In other words, a user may experience dry mouth without suffering from other sleep disorders.

It should further be understood that, while a patient may experience dry mouth from prolonged oral respiration while sleeping, according to other exemplary embodiments, the patient may experience dry mouth conditions and such conditions may be diagnosed while the patient is awake. During a dry mouth diagnosis, a patient may be observed while awake to identify a preference for oral respiration over nasal respiration. For example, a patient having enlarged or swollen adenoids may experience restrictions or obstructions for nasal respiration and may therefore naturally prefer oral respiration. Such condition may be determined by feeling the patient's neck proximate the adenoids to identify enlargement relative to the patient's healthy state and/or relative to an average patient's adenoid size. The condition may further be identified by taking and analyzing an X-ray or visually inspecting the nasal passage for blockage with a telescope. If enlarged adenoids or other blockage for nasal respiration is identified, a diagnosis of dry mouth may be made.

In a second step 104 of the method 100 of treating dry mouth, a patient or other person removes a face strip from a sterile packaging. The face strip may be any face strip 40, 80, 90, as discussed above. While the following discussion refers to the face strip 40, including the adhesive layer 41 and the mesh layer 45 disposed on the adhesive layer 41, it should be understood that these references may apply to similar corresponding features of the face strip 80, 90. The patient may discard the sterile packaging or may keep the packaging available for subsequent (e.g., non-sterile) re-use after the user is finished wearing the face strip.

In a third step 106 of the method 100 of treating dry mouth, the patient or other person removes an adhesive backing from the front surface 42 of the face strip 40, exposing adhesive on the front surface 42 of the adhesive layer 41 to the user and/or the environment. Similarly to the packaging, discussed in the second step 104, in the third step 106 the user may discard the adhesive backing or may keep the adhesive backing available for subsequently re-applying to the adhesive on the front surface 42 of the adhesive layer 41 in order to protect the adhesive from drying or picking up contaminants when the face strip 40 is not in use.

In a fourth step 108 of the method 100 of treating dry mouth, the patient or other person applies the first surface 42 of the adhesive layer 41 directly to at least one of the patient's lips and/or face. As discussed above, when the adhesive layer 41 is disposed on the user's mouth, the adhesive securely attaches the face strip 40 to one or more of the user's lips, upper and/or lower vermillion, and/or face proximate and surrounding the user's mouth. According to another exemplary embodiment, at least a portion of the face strip 40 may be securably attached to an inner surface of the user's upper and/or lower lips, such that the face strip 40 is exposed directly to the user's mouth cavity. According to another exemplary embodiment, the face strip 40 may be securably attached at least one internal portion of the user's mouth and at least one external portion of the user's mouth. While the present application describes applying the face strip 40 to the user's mouth, it should be understood that according to other exemplary embodiments, the face strip 40 may be configured to cover the user's nostrils in addition to or instead of the mouth in substantially the same way as discussed above with respect to the user's mouth. According to yet another exemplary embodiment, the user may apply at least one strip to the mouth and at least to the user's nostril or nostrils.

During the fourth step 108, before the adhesive layer 41 is applied to the user's mouth, the user aligns the opening 43 to a position where the user's upper and lower lips engage or a position between the upper and lower lips. For example, prior to applying the face strip 40, the user may press his or her lips together in a fully closed position. According to another exemplary embodiment, at least a portion of the upper and lower lips may be separated (e.g., spaced apart) slightly, such that the opening 43 is exposed to the user's mouth cavity. In either configuration, the user's jaw may be positioned in a relaxed condition, such that the face strip 40 does not apply a biasing force on the user's jaw while the user is awake.

After the face strip 40 is applied to the user's mouth, the face strip 40 covers substantially all of the user's mouth. According to an exemplary embodiment, the fourth step 108 includes forming a seal (e.g., a semi-secure seal) over the user's mouth with the face strip 40. In other words, the adhesive layer 41 forms a substantially complete circumference (i.e., ring) at or around the user's lips, in which the adhesive layer 41 engages the user's lips or face at all points along the circumference. For example, if the face strip 40 did not include the opening 43, the seal between the adhesive layer 41 and the user's mouth may completely prevent oral respiration. In this configuration, the seal may be formed on an external portion of the user's lips.

After the face strip 40 is fully applied, the method 100 further includes a fifth step 110, which includes engaging in a controlled respiratory activity. For example, the respiratory activity may include sleeping, which is controlled by the face strip 40 to induce nasal respiration and minimize or prevent oral respiration. According to another exemplary embodiment, the respiratory activity is breathing while awake in either a regulated or unregulated breathing rate. For example, the face strip 40 may be worn during breathing exercises to maintain a desired respiratory rate.

After the controlled respiratory activity is established, the method 100 further includes a sixth step 112, which includes using the face strip 40 to maintain a stable breathing pattern by promoting nasal respiration. As discussed above, the face strip 40 induces nasal respiration by increasing the resistance of breathing through the opening 43 to a level greater than a resistance from nasal respiration. For example, the opening 43 may have an area less than an area of one or two nostrils. According to another exemplary embodiment, the face strip 40 maintains the user's lips in a substantially closed position (e.g., complete resistance), such that substantially all of the controlled respiration is nasal respiration. The higher resistance in the mouth (e.g., at the face strip 40)

relative to the nasal passage forces the user's tongue into sealing contact with the upper palate or other portion of the user's mouth cavity, maintaining nasal respiration. The face strip 40 may further hold the user's jaws in a relaxed closed position, thereby preventing the weight of the user's jaw from separating the user's lips to an open position. Notably, by affixing the face strip 40 to at least one of the user's upper vermillion and a lower vermillion, such that the upper lip, the lower lip, and the mouth of the user are covered by the face strip 40, the face strip 40 ensures that the user's tongue does not relax during sleep, opening up oral respiration. The face strip 40 holds the mouth of the user in a naturally closed posture and thereby facilitates nasal respiration by the user.

When the user is finished with the controlled respiratory activity, the method 100 further includes a seventh step 114, in which the user removes the face strip 40. For example, the user may remove the face strip 40 after he or she wakes up from a sleep session during which the face strip 40 is worn. The face strip 40 may be removed by pulling on the removal tabs 46, as discussed above, or may be removed in any other suitable manner.

After the face strip 40 is removed in the seventh step 114 as well as at other points during the method 100, the method 100 reduces an incidence of the dry mouth condition in the user below a predetermined threshold relative to an incidence of the dry mouth condition in the user prior to any treatment for dry mouth. According to another exemplary embodiment, the method 100 includes reducing an incidence of dry mouth in the user relative to treatment without using the face strip 40 as disclosed herein. In one example, the method 100 includes reducing an incidence of dry mouth in the user by more than approximately 50% relative to treatment without using the face strip 40. In another example, the method 100 further includes reducing an incidence of dry mouth in a user by approximately 90% relative to treatment without using the face strip 40. In yet another example, the method 100 further includes reducing an incidence of dry mouth in the user to a clinically insignificant level (e.g., frequency). In another example, the incidence of dry mouth, whether before or during treatment, is based on a subjective measure of the incidence of dry mouth in the user.

While the method 100 is configured for use in a user who does not suffer from sleep apnea, according to an exemplary embodiment, the method 100 may further include using the face strip 40 in combination with a MAD, CPAP, or other device configured to induce nasal respiration to treat sleep apnea. For example, the method 100 may optionally include an eight step 116, which includes inserting a MAD or other device in the user's mouth prior to applying the face strip 40 thereto. The MAD may be configured as described above, with respect to FIGS. 1-3. Because the MAD is inserted into the user's mouth, the MAD should be inserted before the face strip is applied 40 and may be removed after the face strip 40 is removed.

Figure 19:
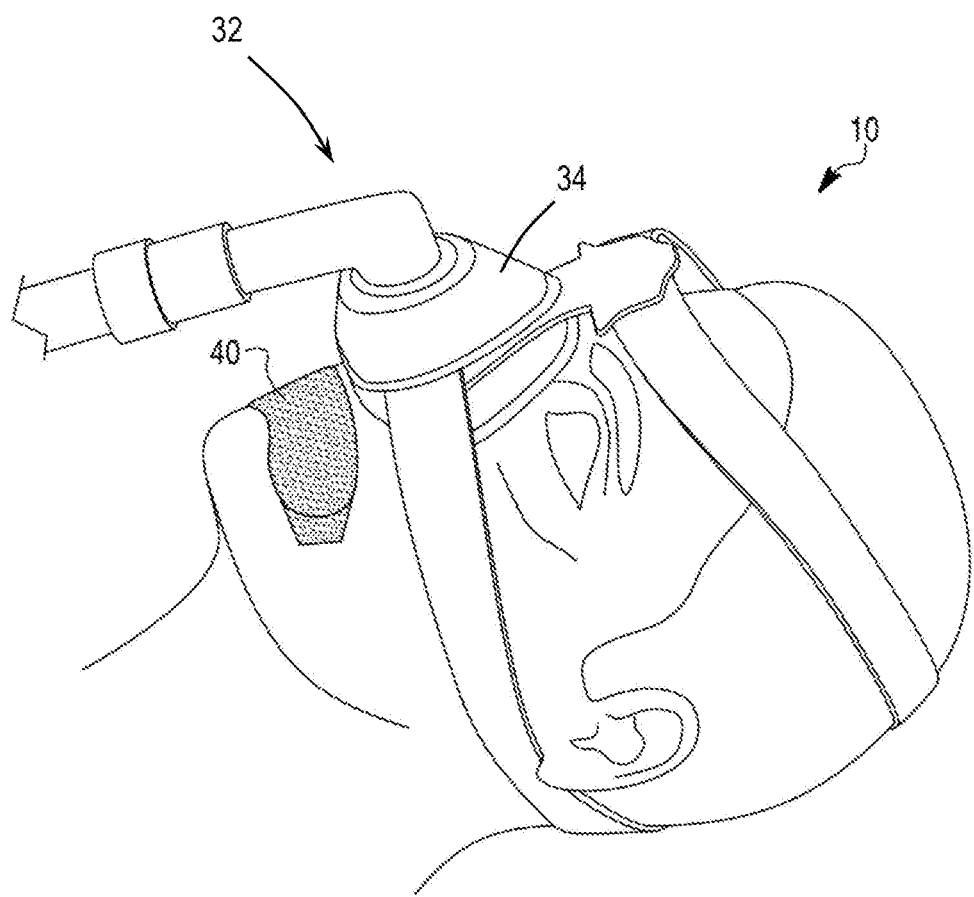
FIG. 19 is a perspective view of a combination of a CPAP device and a face strip.

Similarly, the method 100 may optionally further include a ninth step 118, which includes applying a CPAP or other device to the user's face in order to treat sleep apnea. This step may be in addition to or in place of inserting the MAD, as described in the eight step 116. The CPAP device may be substantially the same as described above with respect to FIGS. 4-6. For example, as shown in FIG. 19, the user 10 is shown with the face strip 40 covering his or her mouth as well as the nasal mask 34 of the CPAP device 32 covering the nose. However, it should be understood that the CPAP device 32 may include the nasal pillow 37 and/or the full face mask 38 or other CPAP device 32.

Figure 16:
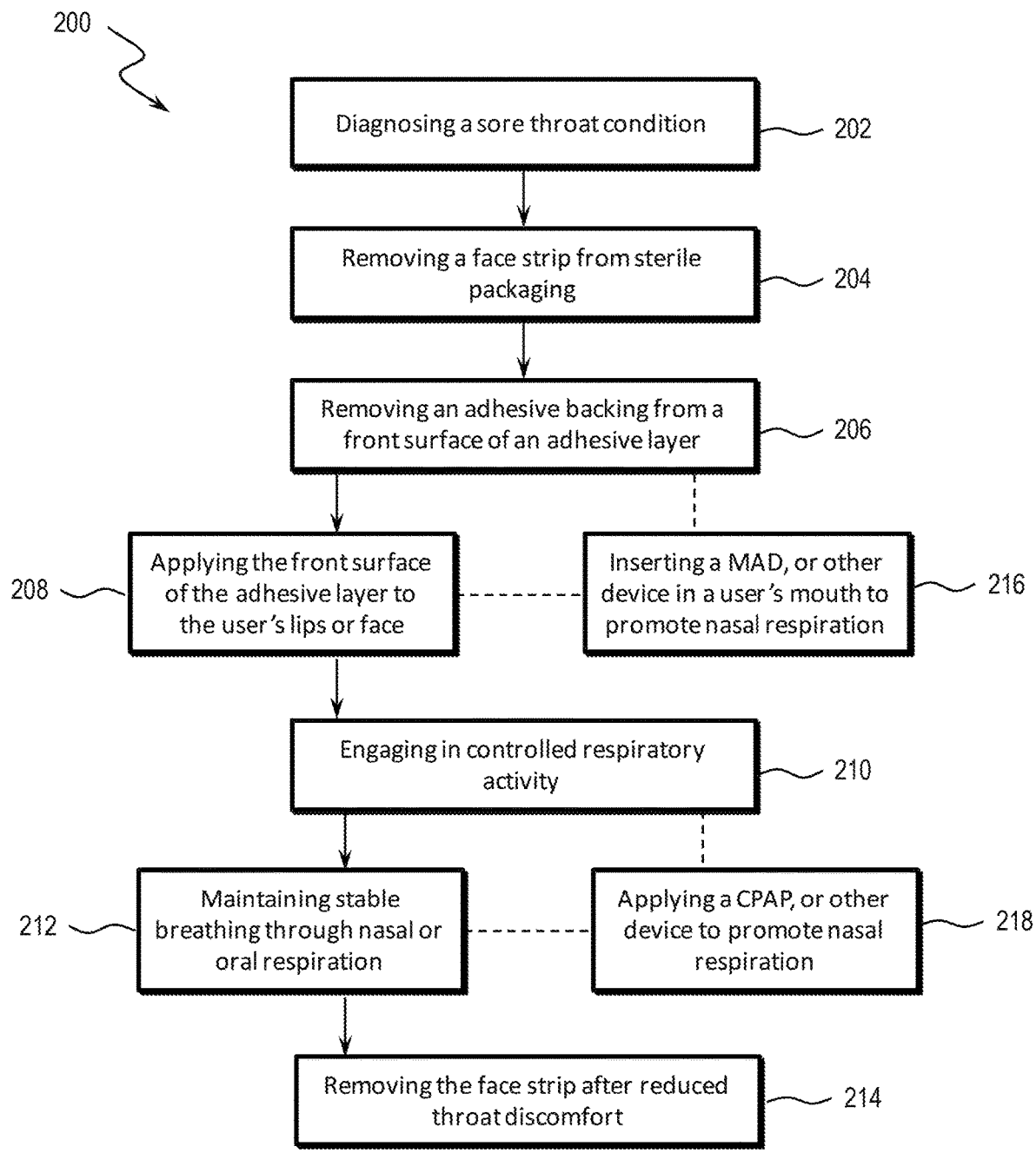
FIG. 16 shows a method of treating a sore throat in a patient using a face strip, according to an exemplary embodiment.

Referring now to FIG. 16, a method 200 of treating a sore throat is shown according to an exemplary embodiment. With reference to FIG. 16, it should be understood that like elements having like reference numerals may be substantially the same between various methods (e.g., the method 100), except as otherwise described. A sore throat is a condition, which may involve irritation (e.g., swelling, inflammation, rawness, sores, etc.) in a patient's throat. In particular, the irritation may occur proximate a back of the patient's airway. For example, the irritation may be disposed between or proximate the patient's tonsils and larynx. According to another exemplary embodiment, the tonsils themselves may be subject to irritation. According to yet another exemplary embodiment, the irritation may occur in or proximate the patient's esophagus, causing discomfort while swallowing. In each of these situations, the irritation may occur between the patient's mouth cavity and the patient's airway (e.g., extending downstream from the patient's mouth cavity, through the airway, toward the trachea).

The sore throat may be caused by a bacterial or viral infection or may be caused by other factors. For example, lifestyle choices (e.g., use of tobacco, alcohol, or psychoactive drugs), other smoke inhalation, extensive talking or yelling, or other factors may also contribute to a sore throat. Further, a sore throat may develop due to long-term oral respiration (e.g., for approximately 1-8 hours consecutively or non-consecutively). When a patient breathes through an open mouth (e.g., when the individual is snoring), a sore throat may either occur or be exacerbated (i.e., worsen) as moisture is exhaled from airway and out through the open mouth. To remedy a sore throat caused by any of these situations, limiting or preventing oral respiration by maintaining the mouth in a closed position will help retain moisture in the throat, preventing a sore throat from worsening or preventing a sore throat from developing in the first place. Specifically, by inhibiting oral respiration, a user engages in primarily or exclusively nasal respiration. Nasal respiration may be less forceful (e.g., slower) than oral respiration, preventing as much moisture from being exhaled by the patient.

Another cause of irritation that leads to a sore throat may include the introduction of irritants and foreign particulates (e.g., dust, allergens, etc.) to the user's mouth or airway from ambient air. For example, seasonal allergies may be exacerbated by the inhalation of pollen or other allergens by a patient, causing irritation and a sore throat. During nasal respiration, nose hairs proximate a patient's nostrils serve as a natural filter, adhering to and removing at least a portion of the foreign particulates before they pass completely through the nasal passage into the patient's airway. By using a face strip 40 to promote exclusively nasal respiration, a patient may limit the introduction of foreign particulates or other matter, reducing or preventing irritation causing a sore throat. According to another exemplary embodiment, the mesh layer 45 also acts as a filter as the patient breathes through the opening 43 and the mesh layer 45 covering the opening 43. Even if the patient inadvertently engages in oral respiration, the presence of the mesh layer 45 filters the air similarly to the patient's nose hairs, preventing the foreign particulates or other matters from entering the airway and causing irritation as discussed above.

Referring still to FIG. 16, the method 200 includes a first step 202, including diagnosing a sore throat condition. A patient may identify a sore throat due to difficulty or discomfort breathing or swallowing. The sore throat may further be diagnosed by visually observing the patient's airway, mouth, and/or esophagus for at least one of redness, swelling, and/or sores. According to various exemplary embodiments, the sore throat may be diagnosed using any of the methods discussed above with respect to the dry mouth condition, and at least some of the symptoms of the dry mouth condition may be interpreted to indicate a sore throat condition is present.

As discussed above, the method 200 includes a second step 204, which may be substantially the same the second step 104, a third step 206, which may be substantially the same as the third step 106, a fourth step 208, which may be substantially the same as the fourth step 108, and a fifth step 210, which may be substantially the same as the fifth step 110.

The method 200 further includes a sixth step 212, which includes using the face strip 40 to maintain a stable breathing pattern. According to an exemplary embodiment, the breathing pattern may include primarily or exclusively nasal respiration. For example, the patient may inhale and/or exhale a larger volume of air through the nasal passage than through the mouth or may inhale and/or exhale exclusively through the nasal passage.

As discussed above with respect to FIG. 15, the face strip 40 induces nasal respiration in substantially the same way by increasing the resistance of breathing through the opening 43 to a level greater than a resistance from nasal respiration. For example, the opening 43 may have an area less than an area of one or two nostrils. According to another exemplary embodiment, the face strip 40 maintains the user's lips in a substantially closed position (e.g., complete resistance), such that substantially all of the controlled respiration is nasal respiration. The higher resistance in the mouth (e.g., at the face strip 40) relative to the nasal passage forces the user's tongue into sealing contact with the upper palate or other portion of the user's mouth cavity, maintaining nasal respiration. The face strip 40 may further hold the user's jaws in a relaxed closed position, thereby preventing the weight of the user's jaw from separating the user's lips to an open position. Notably, by affixing the face strip 40 to at least one of the user's upper vermillion and a lower vermillion, such that the upper lip, the lower lip, and the mouth of the user are covered by the face strip 40, the face strip 40 ensures that the user's tongue does not relax during sleep, opening up oral respiration. The face strip 40 holds the mouth of the user in a naturally closed posture and thereby facilitates nasal respiration by the user.

According to another exemplary embodiment, in the sixth step 212, the patient may engage in exclusively oral respiration or a mixture of both oral respiration and nasal respiration. For example, the patient may inhale and/or exhale a larger volume of air through oral respiration than through nasal respiration. During oral respiration, the patient filters foreign particulates through the mesh layer 45 before air is inhaled through the opening 43 into the patient's mouth. The foreign particulates are either captured by the mesh layer 45 or are prevented from passing into the mesh layer 45 due to the structure of the mesh layer 45.

When the user is finished with the controlled respiratory activity, the method 200 further includes a seventh step 214, in which the user removes the face strip 40. For example, the user may remove the face strip 40 after he or she wakes up from a sleep session during which the face strip 40 is worn. The face strip 40 may be removed by pulling on the removal tabs 46, as discussed above, or may be removed in any other suitable manner.

After the face strip 40 is removed in the seventh step 214 as well as at other points during the method 200, the method 200 reduces an incidence of the sore throat condition in the user below a predetermined threshold relative to an incidence of the sore throat condition in the user prior to any treatment for a sore throat. According to another exemplary embodiment, the method 200 includes reducing an incidence of a sore throat in the user relative to treatment without using the face strip 40 as disclosed herein. In one example, the method 200 includes reducing an incidence of a sore throat in the user by more than approximately 50% relative to treatment without using the face strip 40. In another example, the method 200 further includes reducing an incidence of a sore throat in a user by approximately 90% relative to treatment without using the face strip 40. In yet another example, the method 200 further includes reducing an incidence of a sore throat in the user to a clinically insignificant level, such that the user does not perceive a sore throat, even if the throat is visibly inflamed. In another example, the incidence of a sore throat, whether before or during treatment, is based on a subjective measure of the incidence of a sore throat in the user.

It should further be understood that not only may the face strip 40 be used to reduce irritation in the throat, but it may further be used by a patient to prevent irritation in the first place. For example, as described above, the face strip 40 may be used to limit or prevent effects from seasonal allergies. In one example of this configuration, inhalation of foreign particulates is reduced by at least approximately 50% relative to oral respiration without the face strip 40. In another example, inhalation of foreign particulates is reduced by at least approximately 90%. In yet another example, inhalation of foreign particulates is reduced to a clinically insignificant level, such that the patient does not display signs of seasonal allergies or other breathing condition.

With respect to a MAD or CPAP device, the method 200 may be performed in combination with these or other devices. For example, the method 200 may include an eight step 216, which may be substantially the same as the eighth step 116, and/or may include a ninth step 218, which may be substantially the same as the ninth step 118.

Figure 17:
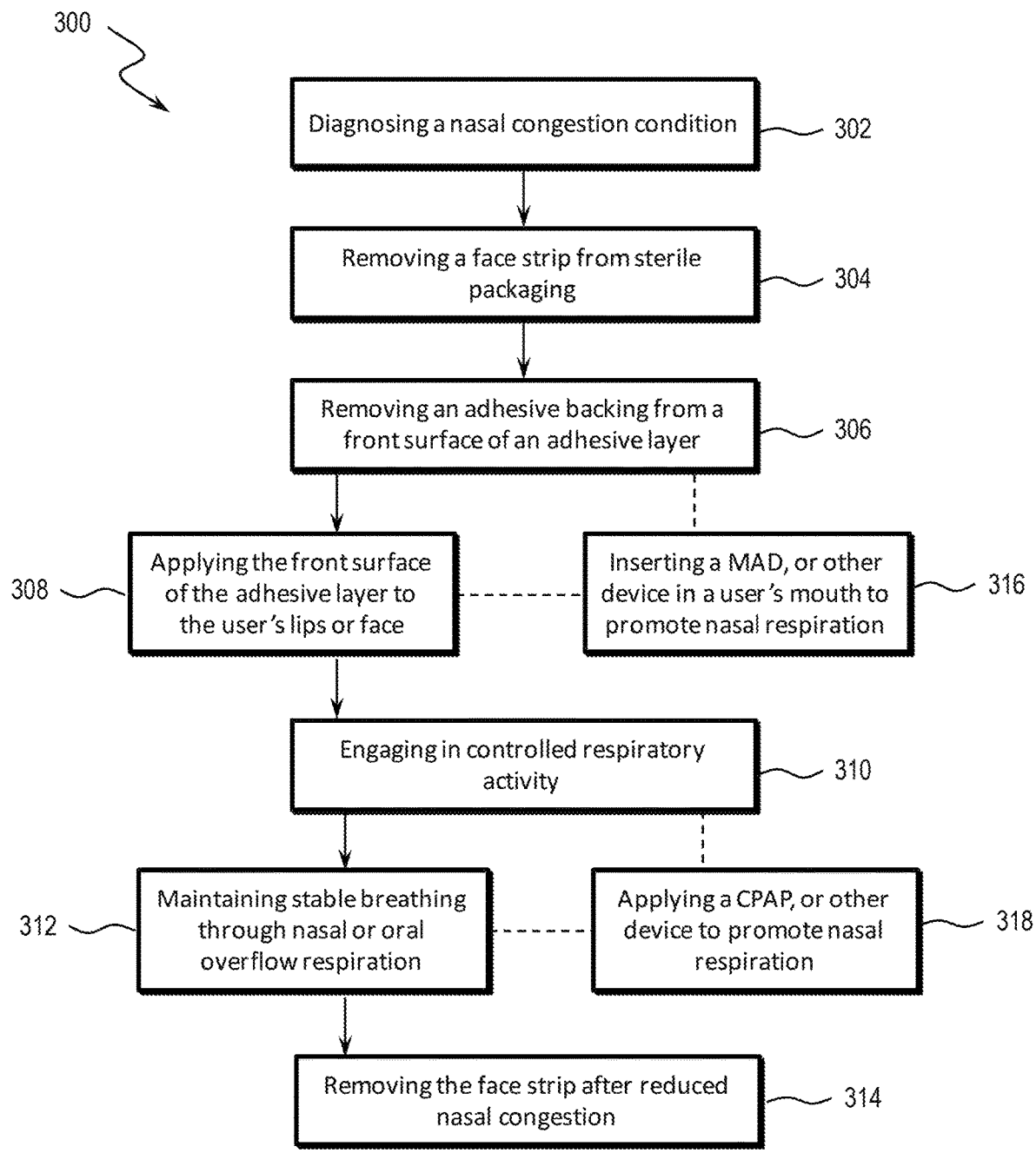
FIG. 17 shows a method of treating nasal congestion in a patient using a face strip, according to an exemplary embodiment.

Referring now to FIG. 17, a method 300 of treating nasal congestion is shown according to an exemplary embodiment. With reference to FIG. 17, it should be understood that like elements having like reference numerals may be substantially the same between various methods (e.g., the methods 100, 200), except as otherwise described. Nasal congestion is a condition, which may involve a pressure build-up in a patient's sinus cavity and/or nasal passage, such that the nasal passage, adjacent tissue, and/or blood vessel become swollen with excess fluid. According to other exemplary embodiments, the patient may further include inflammation or other irritation of the tissue lining the nasal passage. The fluid build-up and inflammation results in a constriction of the nasal passage, which thereby inhibits nasal respiration. According to other exemplary embodiments, mucus (e.g., either dried or runny) may fill the nasal passage, blocking at least one of the user's nostrils, and limiting airflow through the nasal passage. It should be further understood that prolonged incidence of nasal congestion may lead to complications, such as post-nasal drip, and may lead to subsequent viral or bacterial infection. Such infections may further cause a sore throat, which may be treated as discussed above.

Nasal congestion may be caused by a bacterial or viral infection or may be caused by other factors. For example, a sinus infection, ear infection, nasal polyps, foreign particulates (e.g., pollen causing seasonal allergies, dust, other allergens, etc.), chemicals, etc. may contribute to nasal congestion, as described above. In some scenarios, a patient may engage in oral inhalation followed by nasal exhalation. In this pattern, the patient inhales particulates without any filter. These particulates may irritate the patient's throat as discussed above, and cause a sore throat to occur. Further, as the patient engages in nasal exhalation, the particulates engage with the nasal passage and cause irritation therein. As the user exhales, the particulate may adhere to the patient's nose hairs, retaining at least a portion of the particulate within the patient's nasal passage, thereby exacerbating nasal congestion. Further, when a patient is already experiencing mild blockage in the nasal passage, the additional introduction of foreign particulates may increase irritation and swelling, further restricting nasal respiration.

To remedy nasal congestion caused by any of these situations, limiting or preventing oral respiration by maintaining the mouth in a closed position will help prevent the introduction of additional irritants through the mouth and into the nasal passage, preventing the irritation from worsening. Specifically, by inhibiting oral respiration, a user engages in primarily or exclusively nasal respiration. By inhaling substantially exclusively through nasal respiration, the user's nasal passage naturally filters the air with nose hairs proximate the nostrils, limiting the introduction of foreign particulates to the rest of the nasal passage.

According to another exemplary embodiment, the patient may continue to engage in oral inhalation and nasal exhalation. When the patient is wearing the face strip 40 and engages in oral inhalation, the mesh layer 45 acts as a filter as the patient breathes through the opening 43 and the mesh layer 45 covering the opening 43. Even if the patient inadvertently engages in oral respiration, the presence of the mesh layer 45 filters the air similarly to the patient's nose hairs, preventing the foreign particulates or other matters from entering the airway and subsequently passing through the nasal passage, causing irritation therein as discussed above.

Referring still to FIG. 17, the method 300 includes a first step 302, including diagnosing a nasal congestion condition. A patient may identify nasal congestion due to difficulty or discomfort breathing through the nasal passage and/or an increase in mucus build-up or discharge from the nasal passage. According to another exemplary embodiment, the diagnosis may be made based on a known pollen or other allergen condition based on a measurement of ambient air or time of year. Nasal congestion may further be diagnosed by visually observing the patient's nasal passage for at least one of mucus build-up, redness, swelling, and/or sores. When accompanying a sinus or other infection, nasal congestion may further be indicated by a fever in the patient. According to various exemplary embodiments, nasal congestion may be diagnosed using any of the methods discussed above with respect to the dry mouth or sore throat conditions, and at least some of the symptoms of these conditions may be interpreted to indicate nasal congestion is present.

As discussed above, the method 300 includes a second step 304, which may be substantially the same the second step 104, a third step 306, which may be substantially the same as the third step 106, a fourth step 308, which may be substantially the same as the fourth step 108, and a fifth step 310, which may be substantially the same as the fifth step 110.

The method 300 further includes a sixth step 312, which includes using the face strip 40 to maintain a stable breathing pattern. According to an exemplary embodiment, the breathing pattern may include primarily or exclusively nasal respiration. For example, the patient may inhale and/or exhale a larger volume of air through the nasal passage than through the mouth or may inhale and/or exhale exclusively through the nasal passage.

Similarly to the discussion above with respect to FIG. 15, the face strip 40 induces nasal respiration in substantially the same way by increasing the resistance of breathing through the opening 43 to a level greater than a resistance from nasal respiration. For example, the opening 43 may have an area less than an area of one or two nostrils. According to another exemplary embodiment, the face strip 40 maintains the user's lips in a substantially closed position (e.g., complete resistance), such that substantially all of the controlled respiration is nasal respiration. The higher resistance in the mouth (e.g., at the face strip 40) relative to the nasal passage forces the user's tongue into sealing contact with the upper palate or other portion of the user's mouth cavity, maintaining nasal respiration. The face strip 40 may further hold the user's jaws in a relaxed closed position, thereby preventing the weight of the user's jaw from separating the user's lips to an open position. Notably, by affixing the face strip 40 to at least one of the user's upper vermillion and a lower vermillion, such that the upper lip, the lower lip, and the mouth of the user are covered by the face strip 40, the face strip 40 ensures that the user's tongue does not relax during sleep, opening up oral respiration. The face strip 40 holds the mouth of the user in a naturally closed posture and thereby facilitates nasal respiration by the user.

During primarily or exclusively nasal respiration with the face strip 40, nasal respiration itself may reduce or prevent mucus buildup. Specifically, goblet cells, which secrete mucus, receive signals to produce mucus when the brain is losing carbon dioxide too quickly, in order to restrict the airway and slow the rate of exhalation. As a result, the slower rate of exhalation during nasal respiration prevents the activation of the goblet cells and therefore prevents or reduces the formation of mucus, clearing the nasal passage. As a result, nasal respiration or at least restricted oral respiration reduces carbon dioxide loss by slowing exhalation, thereby reducing mucus formation and relieving nasal congestion.

According to another exemplary embodiment, in the sixth step 312, the patient may engage in exclusively oral respiration or a mixture of both oral respiration and nasal respiration. For example, the patient may inhale and/or exhale a larger volume of air through oral respiration than through nasal respiration. During oral respiration, the patient filters foreign particulates through the mesh layer 45 before air is inhaled through the opening 43 into the patient's mouth. The foreign particulates are either captured by the mesh layer 45 or are prevented from passing into the mesh layer 45 due to the structure of the mesh layer 45.

According to another exemplary embodiment, in the sixth step 312, the patient may engage in a sequence of oral and nasal respiration, or a varying mixture of both oral and nasal respiration. For example, the patient may inhale a larger volume of air through oral inhalation than in nasal inhalation or may exclusively inhale through oral inhalation. The patient may then exhale a larger volume of air through nasal exhalation than in oral exhalation or may exclusively exhale through nasal exhalation. In this configuration, the breathing pattern helps prevent the introduction of particulates to the user's nasal passage and further promotes the movement of mucus out of the patient's nasal passage, rather than toward the patient's airway due to the one-directional outward flow in the nasal passage.

According to yet another exemplary embodiment, the face strip 40 is configured to promote predominantly or exclusively nasal respiration. For example, the face strip 40 may cause nasal respiration as provided with respect to FIGS. 15 and 16, discussed above. However, in certain scenarios, the dry mouth condition and/or the sore throat condition may be coupled with a corresponding nasal congestion condition. For example, due to similar causes of each of the breathing conditions, this combination may arise after the patient has fallen asleep and is unaware of the increasing nasal constriction. The swelling of the nasal passage and/or the formation of mucus therein reduces the area available for nasal respiration. For example, when the available area in the nasal passage falls below the area of the opening 43 in the face strip 40, the resistance in the nasal passage increases above the resistance in the mouth cavity, forcing the user's tongue rearward and exposing the user's mouth for oral respiration. In this configuration, the face strip 40 and more specifically, the opening 43 therein serves as an overflow (i.e., backup, reserve, etc.) opening for passing air for respiration when nasal respiration provides more resistance than oral respiration or is not possible due to excessive constriction.

When the user is finished with the controlled respiratory activity, the method 300 further includes a seventh step 314, in which the user removes the face strip 40. For example, the user may remove the face strip 40 after he or she wakes up from a sleep session during which the face strip 40 is worn. The face strip 40 may be removed by pulling on the removal tabs 46, as discussed above, or may be removed in any other suitable manner.

After the face strip 40 is removed in the seventh step 314 as well as at other points during the method 300, the method 300 reduces an incidence of nasal congestion in the user below a predetermined threshold relative to an incidence of nasal congestion in the user prior to any treatment for nasal congestion. For example, a volume of mucus in the nasal passage and/or swelling of the tissue in the nasal passage may be reduced after or because of the face strip 40. According to another exemplary embodiment, the method 300 includes reducing an incidence of nasal congestion in the user relative to treatment without using the face strip 40 as disclosed herein. In one example, the method 300 includes reducing an incidence of nasal congestion in the user by more than approximately 50% relative to treatment without using the face strip 40. In another example, the method 300 further includes reducing an incidence of nasal congestion in a user by approximately 90% relative to treatment without using the face strip 40. In yet another example, the method 300 further includes reducing an incidence of nasal congestion in the user to a clinically insignificant level, such that the user does not perceive nasal congestion, even if the nasal passage is visibly inflamed, and/or contains mucus (e.g., runny mucus). In another example, the incidence of nasal congestion, whether before or during treatment, is based on a subjective measure of the incidence of nasal congestion in the user.

It should further be understood that not only may the face strip 40 be used to reduce irritation in the nasal passage, but it may further be used by a patient to prevent irritation in the first place. For example, as described above, the face strip 40 may be used preemptively to limit or prevent effects from seasonal allergies. In one example of this configuration, inhalation of foreign particulates is reduced by at least approximately 50% relative to oral respiration without the face strip 40. In another example, inhalation of foreign particulates is reduced by at least approximately 90%. In yet another example, inhalation of foreign particulates is reduced to a clinically insignificant level, such that the patient does not display signs of seasonal allergies or other breathing condition.

With respect to a MAD or CPAP device, the method 300 may be performed in combination with these or other devices. For example, the method 300 may include an eight step 316, which may be substantially the same as the eighth step 116, and/or may include a ninth step 318, which may be substantially the same as the ninth step 118.

Figure 18:
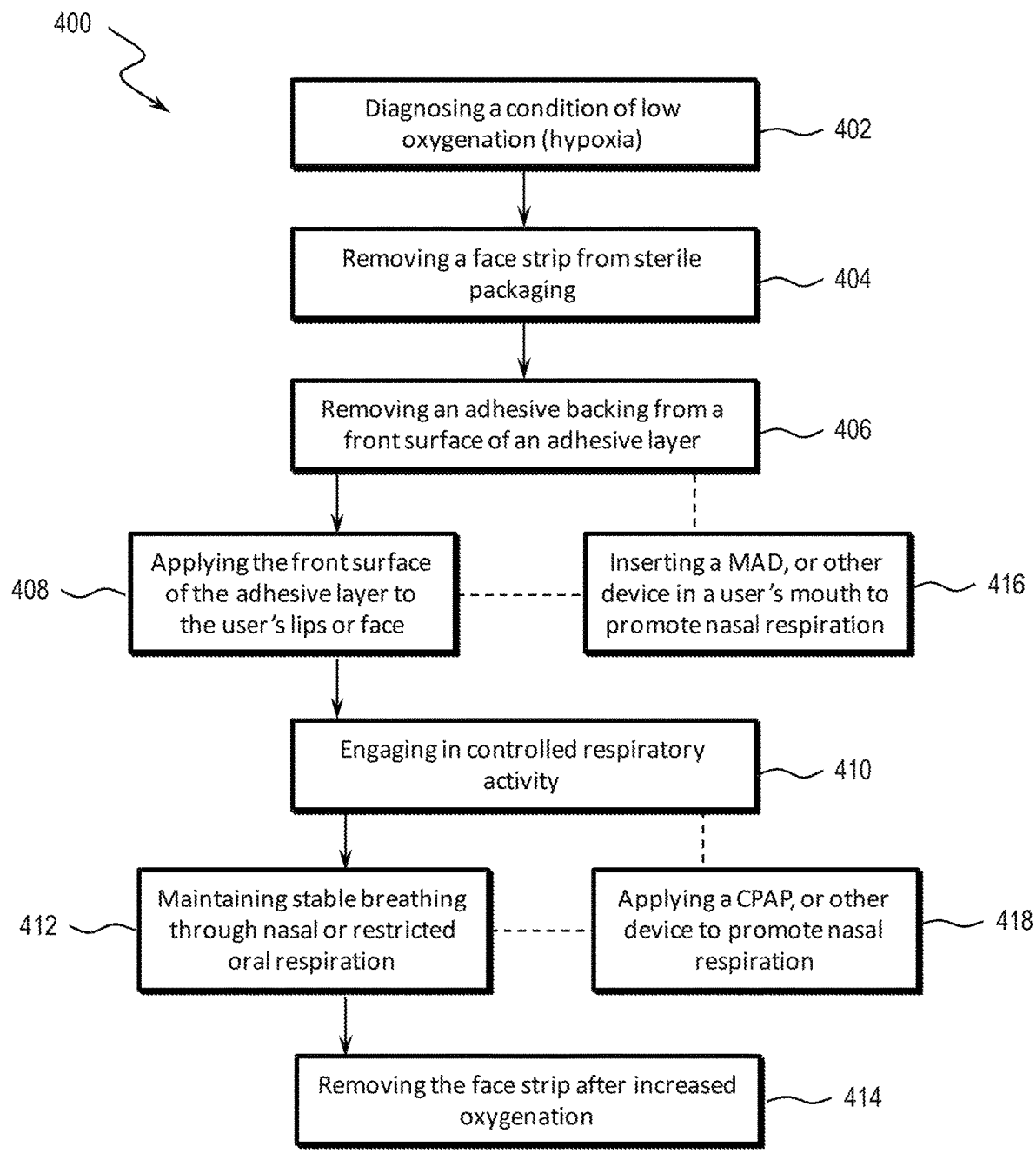
FIG. 18 shows a method of treating hypoxia in a patient using a face strip, according to an exemplary embodiment.

Referring now to FIG. 18, a method 400 of treating hypoxia is shown according to an exemplary embodiment. With reference to FIG. 18, it should be understood that like elements having like reference numerals may be substantially the same between various methods (e.g., the methods 100, 200, 300), except as otherwise described. Hypoxia is a condition, which may occur when portions of a patient's body, often at the extremities, do not receive sufficient oxygen. Hypoxia may lead to a loss of sensation and temporary discoloration, or in extreme situations of prolonged hypoxia, gangrene at the affected portions.

Hypoxia may occur when there is insufficient consumption of oxygen and subsequent conversion to carbon dioxide. Insufficient oxygen consumption is exacerbated by limiting the volume of oxygen inhaled and/or the duration of time the oxygen is in the lungs, thereby limiting the quantity of oxygen that may pass through the pulmonary and cardiovascular systems and be converted into carbon dioxide. As a result, hypoxia may be treated by increasing the time between inhalation and exhalation to allow a larger volume of the oxygen in a given breath to be passed through the patient's pulmonary and cardiovascular systems. Specifically, to remedy hypoxia, resistance to exhalation may be increased, forcing the patient to hold air in his or her lungs for a longer period of time, promoting additional oxygenation.

Referring still to FIG. 18, the method 400 includes a first step 402, including diagnosing a hypoxia condition. Hypoxia may be diagnosed by measuring a patient's oxygen level at various portions of the body. For example, a pulse oximeter may be placed at a known location on the patient, including at least one of a patient's finger, hand, wrist, toe, heal, foot, etc. and may take a measurement at that known location. An oxygen level (e.g., a percentage of oxygen in the blood) at that known location is measured by the pulse oximeter. If the oxygen level is below a pre-determined threshold level, the patient is diagnosed with hypoxia. Further, an initial respiration rate (e.g., volume flow rate during inhalation and/or exhalation) may be measured without a face strip 40 present, including conditions of nasal-only respiration, oral-only respiration, and/or a combination of nasal and oral respiration. According to other exemplary embodiments, an oxygen level may be measured in other ways. According to yet another exemplary embodiment, hypoxia may be diagnosed based on visual inspection of the patient. For example, discoloration of at least one of the patient's fingers, hands, toes and/or feet, in which the portion of the patient appears darker (e.g., bluish), may serve as a visual indication that there is insufficient oxygen in the blood.

As discussed above, the method 400 includes a second step 404, which may be substantially the same the second step 104, a third step 406, which may be substantially the same as the third step 106, a fourth step 408, which may be substantially the same as the fourth step 108, and a fifth step 410, which may be substantially the same as the fifth step 110.

The method 400 further includes a sixth step 412, which includes using the face strip 40 to maintain a stable breathing pattern. According to an exemplary embodiment, the breathing pattern may include primarily or exclusively nasal respiration. For example, the patient may inhale and/or exhale a larger volume of air through the nasal passage than through the mouth or may inhale and/or exhale exclusively through the nasal passage.

Similarly to the discussion above with respect to FIG. 15, in the method 400, the face strip 40 induces nasal respiration in substantially the same way by increasing the resistance of breathing through the opening 43 to a level greater than a resistance from nasal respiration. For example, the opening 43 may have an area less than an area of one or two nostrils. According to another exemplary embodiment, the face strip 40 maintains the user's lips in a substantially closed position (e.g., complete resistance), such that substantially all of the controlled respiration is nasal respiration. The higher resistance in the mouth (e.g., at the face strip 40) relative to the nasal passage forces the user's tongue into sealing contact with the upper palate or other portion of the user's mouth cavity, maintaining nasal respiration. The face strip 40 may further hold the user's jaws in a relaxed closed position, thereby preventing the weight of the user's jaw from separating the user's lips to an open position. Notably, by affixing the face strip 40 to at least one of the user's upper vermillion and a lower vermillion, such that the upper lip, the lower lip, and the mouth of the user are covered by the face strip 40, the face strip 40 ensures that the user's tongue does not relax during sleep, opening up oral respiration. The face strip 40 holds the mouth of the user in a naturally closed posture and thereby facilitates nasal respiration by the user.

During exclusively nasal respiration, the resistance in the nasal passage is greater than in the patient's mouth without a face strip 40 applied, due to the smaller cross-sectional area of the nasal passage and/or the nostrils relative to the open mouth. As a result of the smaller area, the volume flow rate of air exhaled from the airway, through the nasal passage, is less than a corresponding volume flow rate when exhaling through the mouth, without the face strip 40, or the combination of the nasal passage and the face strip 40. The lower volume flow rate during nasal-only exhalation effectively retains air, and therefore oxygen, in the patient's lungs for a longer duration, increasing the volume of oxygen that passes through the pulmonary and cardiovascular systems.

According to another exemplary embodiment, in the sixth step 412, the patient may engage in exclusively oral respiration. During exclusively oral respiration, the resistance in the mouth cavity is greater than in the patient's mouth without the face strip 40 applied, due to the smaller cross-sectional area of the opening 43 relative to the open mouth. As a result of the smaller area, the volume flow rate of air exhaled from the airway, through the mouth, is less than a corresponding volume flow rate when exhaling through the mouth, without the face strip 40, or the combination of the nasal passage and the face strip 40. The lower volume flow rate during oral-only exhalation effectively retains air, and therefore oxygen, in the patient's lungs, similarly to nasal-only exhalation, increasing the volume of oxygen that passes through the pulmonary and cardiovascular systems. In the configuration, in which the opening 43 is smaller than the exposed area of the patient's nostrils, the face strip 40 further restricts exhalation relative to nasal-only respiration. Specifically, as the opening 43 decreases in size, the duration of holding oxygen in the patient's lungs increases.

According to yet another exemplary embodiment, in the sixth step 412, the patient may engage in a mixture of both oral respiration and nasal respiration. For example, the patient may exhale through the nasal passage as well as the mouth, through the opening 43 in the face strip 40. A cumulative cross-sectional area of the patient's nostrils and the opening 43 is less than a cumulative cross-sectional area of the patient's nostrils and the patient's mouth, when the mouth is in a relaxed, open position, such that the application of the face strip 40 restricts total exhalation airflow when compared to a configuration without the face strip 40. According to another exemplary embodiment, the cumulative cross-sectional area of the patient's nostrils and the opening 43 is less than a cross-sectional area of the patient's mouth in the relaxed, open position, such that the volume flow rate through the combination of nasal respiration and oral respiration through the opening 43 in the face strip 40 is less than the volume flow rate through oral-only respiration without the face strip 40 applied to the patient's mouth.

When the user is finished with the controlled respiratory activity and increased or full oxygenation of the blood is restored, the method 400 further includes a seventh step 414, in which the user removes the face strip 40. For example, the user may remove the face strip 40 after he or she wakes up from a sleep session during which the face strip 40 is worn. The face strip 40 may be removed by pulling on the removal tabs 46, as discussed above, or may be removed in any other suitable manner.

After the face strip 40 is removed in the seventh step 414 as well as at other points during the method 400, the method 400 reduces an incidence of hypoxia (e.g., increasing oxygen in the bloodstream) in the user below a predetermined threshold relative to an incidence of hypoxia in the user prior to any treatment for nasal congestion. For example, an oxygen level in the blood stream may be increased after or because of the face strip 40. According to another exemplary embodiment, the method 400 includes reducing an incidence of hypoxia in the user relative to treatment without using the face strip 40 as disclosed herein. In one example, the method 400 includes reducing an incidence of hypoxia in the user by more than approximately 50% relative to treatment without using the face strip 40. In another example, the method 400 further includes reducing an incidence of hypoxia in a user by approximately 90% relative to treatment without using the face strip 40. In yet another example, the method 400 further includes reducing an incidence of hypoxia in the user to a clinically insignificant level, such that the user does not perceive a lack of oxygen, even if the patient is still experience discoloration or other signs of hypoxia.

With respect to a MAD or CPAP device, the method 400 may be performed in combination with these or other devices. For example, the method 400 may include an eight step 416, which may be substantially the same as the eighth step 116, and/or may include a ninth step 418, which may be substantially the same as the ninth step 118. Notably, one or both of the MDA and CPAP device may increase a volume of oxygen flowing into the patient's lungs. For example, the positive pressure from a CPAP device increases the volume flow rate and total volume of air received at the patient's lungs, and the face strip 40 slows the volume flow rate and frequency of exhalation, allowing for a larger volume of oxygen to be received in the pulmonary and cardiovascular systems within a fixed duration of time (e.g., during each breath).

Figure 20:
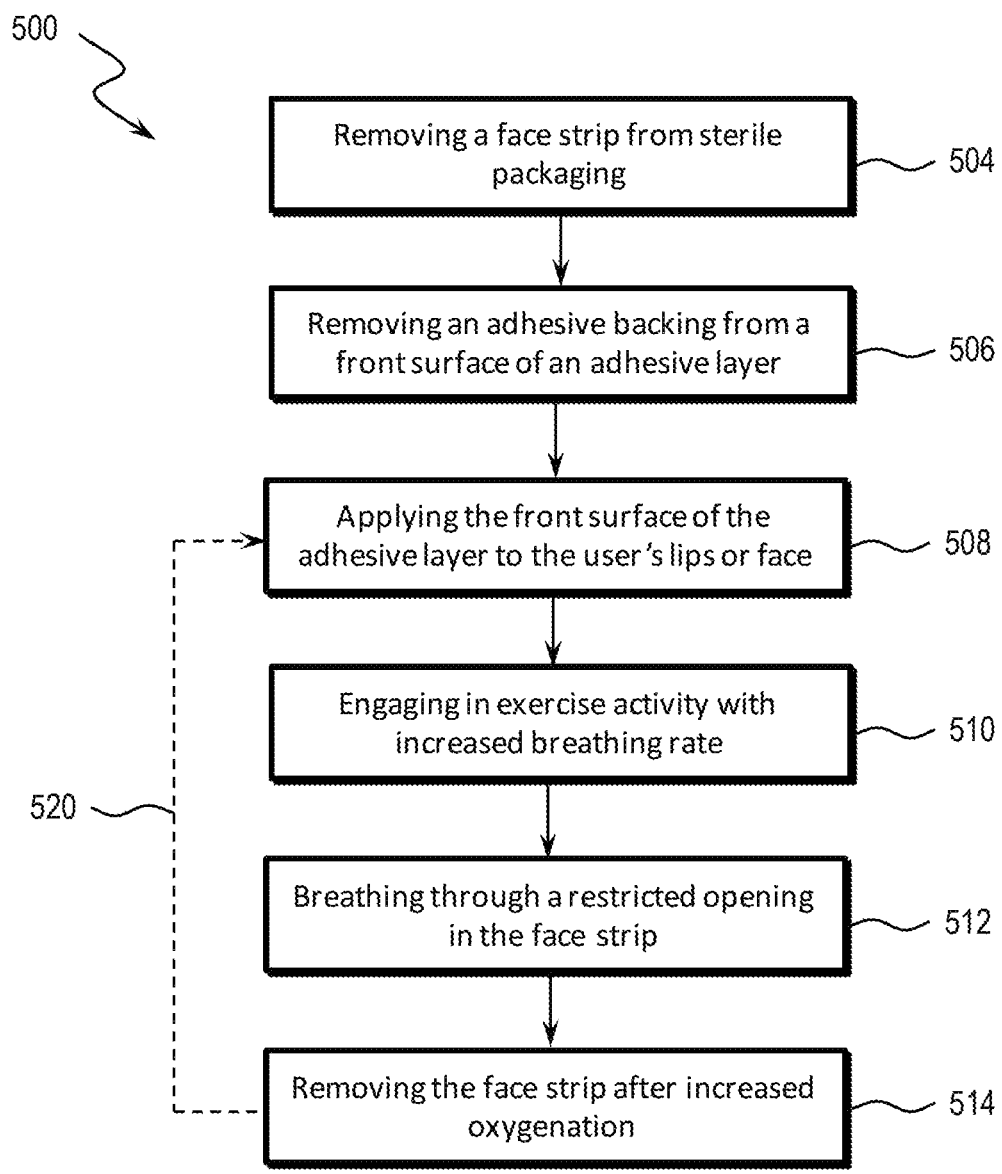
FIG. 20 shows a method of stamina training using a face strip, according to an exemplary embodiment.

Referring now to FIG. 20, a method 500 of training (e.g., endurance, stamina, hypoventilation, hypercapnia training, etc.) is shown according to an exemplary embodiment. With reference to FIG. 20, it should be understood that like elements having like reference numerals may be substantially the same between various methods (e.g., the methods 100, 200, 300, 400), except as otherwise described. During the training method 500, a user utilizes the face strip 40 in order to provide breathing resistance during hypercapnia training. In other words, the resistance provided to the user with the face strip 40 limits the volume flow rate of air into the user's lungs, thereby increasing the percentage of carbon dioxide in the user's pulmonary and cardiovascular systems, relative to the percentage of oxygen present therein.

During exercise activity, a user may exhale too frequently (e.g., hyperventilation), expelling too much carbon dioxide. Specifically, accelerated physical activity causes a user to naturally use oral respiration to try to increase airflow. A reduction of carbon dioxide in the user may be referred to as hypocapnia. Specifically, the presence of carbon dioxide in the user signals to red blood cells to release oxygen to the cells, organs, muscles, and/or tissue. However, when carbon dioxide is exhaled too quickly, there is not as much carbon dioxide in the system to trigger the oxygen release. Hypocapnia may therefore result in breathlessness and quicker exhaustion (e.g., fatigue) and it may be desired to avoid this state by limiting oral respiration, unless specifically engaging in high-intensity interval training ("HIIT") as part of a training regimen.

As shown in FIG. 20, the method 500 includes a first step 504, which may be substantially the same the second step 104 of the method 100, a second step 506, which may be substantially the same as the third step 106 of the method 100, and a third step 508, which may be substantially the same as the fourth step 108 of the method.

The method 500 further includes a fourth step 510, which includes engaging in exercise activity for building up endurance and/or stamina. Specifically, the exercise activity may include cardio-intensive activity (e.g., running, biking, rowing, etc.), with a target heart rate between approximately 90 beats per minute and 170 beats per minute. According to an exemplary embodiment, the target heart rate may be determined between approximately 50%/and 85% of the user's average maximum heart rate, which may be determined or approximated based on the user's age. As the user increases his or her heart rate, a respiration rate increases by a corresponding amount with the heart rate in order to increase a supply of oxygen to the lungs and therefore the pulmonary and cardiovascular systems, satisfying a higher oxygen requirement due to the increased heart rate. For example the user may increase one or both of a breath frequency or a breath volume as his or her heart rate increases.

The method 500 further includes a fifth step 512, which includes breathing through the opening 43 in the face strip 40 while engaging in the exercise activity described with respect to the fourth step 510. According to an exemplary embodiment, the user may inhale substantially exclusively through the opening 43 in the face strip 40 and not through nasal respiration. In this configuration, the opening 43 has a smaller area than an area of the user's mouth when the mouth is in a relaxed, open position. As a result, the user experiences resistance during inhalation. The resistance causes the user to work harder to inhale and therefore the user compensates for this increased resistance by increasing the breathing effort with his or her diaphragm. Exclusive oral inhalation through the face strip 40 may be used to increase the strength of the user's diaphragm as well as the user's lung capacity. After repeated user of the face strip 40 during exercise activity, when the face strip 40 is removed and the user partakes in exercise activity, the user will experience increased lung capacity relative to activity without the face strip 40 prior to the training regime, due to the increased diaphragm strength enabling the user to inhale larger volumes of air. The additional lung capacity will also allow the user to more efficiently oxygenate the pulmonary and cardiovascular systems, improving athletic performance.

According to another exemplary embodiment, if the user does not increase diaphragm effort to maintain a consistent air volume intake as without the face strip 40, inhaling exclusively or primarily through the opening 43 reduces the supply of air and, therefore, oxygen to the user's lungs. This configuration leads to a reduction in the percentage of oxygen present in the pulmonary and cardiovascular systems and a corresponding rise in the percentage of carbon dioxide therein. This condition may be referred to, for example, as hypercapnia and may be utilized to increase acidosis in the body during a training regimen. Notably, such training may be utilized to prepare a user for higher altitudes or freediving. It should be understood that due to the Bohr Effect, over time, the body becomes more tolerant of states of elevated carbon dioxide in the blood and responds by increasing oxygen output from the red blood cells to various cells, organs, muscles, and/or tissues. For example, a buildup of carbon dioxide promotes more oxygenation, including of the brain, muscles, and organs. Further, nasal respiration promotes production of nitric oxide ($NO_2$), a vasolidator, which helps optimize carbon dioxide-oxygen exchange (i.e., homeostasis).

According to another exemplary embodiment, in the fifth step 512, the user may breath through both the opening 43 in the face strip 40 as well as through the nasal passage. Specifically, the user may inhale through the opening 43 and the nasal passage. As discussed above, the combination of the opening 43 and the nostrils provides a smaller cross-sectional area than either the user's open mouth by itself or the combination of the open mouth and the nostrils, such that the volume flow rate of air during combined inhalation is still less than respiration without the face strip 40 affixed to the mouth. According to yet another exemplary embodiment, the user may breathe exclusively through the nasal passage. Specifically, the user may inhale substantially exclusively through the nasal passage, which has a smaller cross-sectional area than the user's open mouth. In this configuration, the face strip 40 holds the user's lips in a closed position, encouraging primarily nasal respiration. As a result of reduced cross-sectional area for inhalation in either of these configurations, resistance during inhalation is increased due to the presence of the face strip 40, requiring the user to use more effort with the diaphragm or reducing the oxygen level in the pulmonary and cardiovascular systems.

According to another exemplary embodiment, in the fifth step 512, the user may exhale substantially exclusively through the opening 43 in the face strip 40 and not through nasal the nasal passage. In this configuration, the volume flow rate during exhalation is less than the volume flow rate for the user without the face strip 40 affixed to the mouth. As a result, the user experiences resistance during exhalation and holds air in his or her lungs longer. By slowing the exhalation with the face strip 40, the body converts more oxygen to carbon dioxide during the exercise activity. According to yet another exemplary embodiment, the user may exhale through both the opening 43 and the nasal passage (e.g., both oral and nasal respiration). However, the combination of the opening 43 and the nostrils provides a smaller area than either the user's open mouth by itself or the combination of the open mouth and the nostrils, such that the volume flow rate of air during combined exhalation is still less than respiration without the face strip 40 affixed to the mouth.

According to yet another exemplary embodiment, the user may exhale substantially exclusively through the nasal passage. In this configuration, as discussed above, the face strip 40 holds the user's lips in a closed position, encouraging primarily nasal respiration. The cross-sectional area of the nasal passage is less than the user's open mouth, such that the volume flow rate through nasal-only exhalation is less than in respiration without the face strip 40, which would allow for oral respiration in combination with or instead of nasal respiration.

It should be understood that depending on the exercise regimen, the user may engage in any one of nasal-only inhalation, oral-only inhalation, or a combination thereof. Similarly, the user may engage in any one of nasal-only exhalation, oral-only exhalation, or a combination thereof. Further, the user may vary between different types of inhalation or exhalation over the course of the exercise regimen and may further provide for different or the same method of exhalation as inhalation.

When the user is finished with the controlled respiratory activity and increased or full oxygenation of the blood is restored, the method 400 further includes a sixth step 514, in which the user removes the face strip 40. For example, the user may remove the face strip 40 after he or she is finished with exercise activity or after only a portion of the exercise activity. The face strip 40 may be removed by pulling on the removal tabs 46, as discussed above, or may be removed in any other suitable manner.

According to an exemplary embodiment, in a seventh step 520, the face strip 40 may be re-applied to the user for continued exercise activity. For example, the face strip 40 may be used intermittently during a specific session of exercise activity, such that the face strip 40 is removed, the user continues exercise activity, and then the face strip 40 is reapplied (e.g., in accordance with the third step 508). In this configuration, the adhesive layer 41 of the face strip is configured to be releasably adhered to the user's lips or face and subsequently removed, while maintaining adhesive force, such that the adhesive layer 41 may be re-adhered during the same exercise session.

While the FIGURES in this application show the face strip 40 covering the user's mouth, it should further be understood that according to an exemplary embodiment, the face strip 40 may be configured to cover the user's nostrils, such that nasal respiration is controlled in substantially the same way as the face strip 40 controls or restricts oral respiration. According to another exemplary embodiment, the face strip 40 may cover the user's mouth and nostrils. According to another exemplary embodiment, one of the mouth or the nostrils may be completely blocked by the face strip 40 or other device and configured to ensure nasal-only or oral-only respiration. According to yet another exemplary embodiment, the user may use a plurality of face strips 40, including a face strip 40 disposed over the mouth and one or more face strips 40, which are either the same or different, disposed over the nostrils.

As utilized herein, the terms "approximately," "about," "substantially," and similar terms are intended to have a broad meaning in harmony with the common and accepted usage by those of ordinary skill in the art to which the subject matter of the disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of this disclosure as recited in the appended claims.

The terms "coupled," "connected," and the like are used herein to mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

References herein to the position of elements (e.g., "top," "bottom," "above," "below," etc.) are merely used to describe the orientation of various elements in the Figures. It should be noted that the orientation of various elements may differ according to other exemplary embodiments and that such variations are intended to be encompassed by the present disclosure.

It is to be understood that although the present invention has been described with regard to embodiments thereof, various other embodiments and variants may occur to those skilled in the art, which are within the scope and spirit of the invention, and such other embodiments and variants are intended to be covered by corresponding claims. Those skilled in the art will readily appreciate that many modifications are possible (e.g., variations in sizes, structures, shapes and proportions of the various elements, mounting arrangements, use of materials, orientations, etc.) without materially departing from the novel teachings and advantages of the subject matter described herein. For example, the order or sequence of any process or method steps may be varied or re-sequenced according to alternative embodiments. Other substitutions, modifications, changes, and omissions may also be made in the design, operating conditions and arrangement of the various exemplary embodiments without departing from the scope of the present disclosure.

With respect to the use of substantially any plural and/or singular terms herein, those having skill in the art can translate from the plural to the singular and/or from the singular to the plural as is appropriate to the context or application. The various singular/plural permutations may be expressly set forth herein for clarity.

What is claimed is:

1. A method for treating a breathing condition, comprising:
    providing a face strip to a patient diagnosed with a breathing condition comprising at least one of dry mouth, sore throat, nasal congestion, or hypoxia, the face strip comprising:
        an adhesive layer having an opening extending therethrough; and
        a mesh layer disposed on a first side of the adhesive layer extending at least over the opening and extending laterally outward from an outer periphery of the adhesive layer to form at least one release tab;
    positioning the face strip by aligning the opening proximate the patient's lips, wherein at least a portion of the patient's lips are spaced apart and the patient's jaw is in a relaxed position;
    applying a second side, the second side opposite to the first side, of the adhesive layer to the patient's mouth;

covering the patient's mouth with the face strip;
providing breathing resistance through the opening greater than breathing resistance from nasal respiration, creating a pressure differential between the patient's mouth and the patient's nasal passage;
permitting greater airflow through the patient's nasal passage relative to the patient's mouth through the opening, limiting or preventing oral respiration; and
increasing nasal respiration with the face strip;
wherein the face strip reduces or prevents the incidence of the breathing condition.

2. The method of claim 1, further comprising adhering the adhesive layer on the patient's lips.

3. The method of claim 1, further comprising conforming the face strip to a curvature of the patient's face.

4. The method of claim 1, wherein the patient is not diagnosed with sleep apnea.

5. The method of claim 1, further comprising applying at least one of a mandibular advancement device or a continuous positive air pressure device to the patient.

6. The method of claim 1, further comprising removing the face strip by pulling the at least one release tab.

7. The method of claim 1, further comprising securing an elastic band coupled to the face strip around the patient's head.

8. A method of breathing training, comprising:
providing a face strip to a user, the face strip comprising:
an adhesive layer having an opening extending therethrough; and
a mesh layer disposed on a first side of the adhesive layer extending at least over the opening and extending laterally outward from an outer periphery of the adhesive layer to form at least one release tab;
positioning the face strip by aligning the opening proximate the user's lips, wherein at least a portion of the user's lips are spaced apart and the user's jaw is in a relaxed position;
applying a second side, the second side opposite to the first side, of the adhesive layer to the user's mouth;
covering the user's mouth with the face strip;
providing breathing resistance through the opening and limiting airflow into and out of the user's lungs;
engaging in a physical activity for building up at least one of endurance or stamina, wherein a target heart rate of the physical activity is approximately between 50% and 85% of the user's average maximum heart rate;
increasing the user's heart rate through the physical activity;
increasing the user's respiration rate, increasing a supply of oxygen to the user's lungs; and
breathing through the opening in the face strip during the physical activity,
wherein the face strip causes at least one of increased breathing effort with the user's diaphragm or reduced oxygen to the user's lungs.

9. The method of claim 8, wherein the opening defines an area less than an area of the user's nostrils.

10. The method of claim 8, wherein the opening defines an area less than approximately 350 square millimeters.

11. The method of claim 10, wherein the area is less than approximately 175 square millimeters.

12. The method of claim 11, wherein the area is less than approximately 125 square millimeters.

13. The method of claim 8, further comprising engaging in nasal respiration.

14. The method of claim 8, further comprising exhaling exclusively through the opening in the face strip.

15. The method of claim 14, further comprising inhaling through a nasal passage.

16. The method of claim 15, further comprising inhaling through the opening in the face strip.

17. The method of claim 8, wherein the physical activity is part of at least one of a hypoventilation or hypercapnia training regimen.

\* \* \* \* \*